(12) United States Patent
Lutgens et al.

(10) Patent No.: US 9,750,717 B2
(45) Date of Patent: Sep. 5, 2017

(54) INHIBITORS OF CD40-TRAF6 INTERACTION

(71) Applicants: Ludwig-Maximilians-Universitaet Muenchen, Munich (DE); Maastricht University, Maastricht (NL); Academisch Ziekenhuis Maastricht, Maastricht (NL)

(72) Inventors: Esther Lutgens, Munich (DE); Christian Weber, Munich (DE); Gerry Nicolaes, Sint Geertruid (NL)

(73) Assignees: LUDWIG-MAXIMILIANS-UNIVERSITÄT MÜNCHEN, München (DE); MAASTRICHT UNIVERSITY, Maastricht (NL)

( * ) Notice: Subject to any disclaimer, the term of this patent is extended or adjusted under 35 U.S.C. 154(b) by 0 days.

(21) Appl. No.: 15/019,581

(22) Filed: Feb. 9, 2016

(65) Prior Publication Data

US 2016/0228408 A1 Aug. 11, 2016

Related U.S. Application Data

(62) Division of application No. 14/417,708, filed as application No. PCT/EP2013/067714 on Aug. 27, 2013, now Pat. No. 9,408,829.

(30) Foreign Application Priority Data

Aug. 27, 2012 (EP) .................................. 12181862

(51) Int. Cl.
| | | |
|---|---|---|
| *A61K 31/381* | (2006.01) | |
| *C07D 333/22* | (2006.01) | |
| *C07C 251/24* | (2006.01) | |
| *C07C 251/26* | (2006.01) | |
| *C07D 307/52* | (2006.01) | |
| *A61K 31/137* | (2006.01) | |
| *A61K 31/341* | (2006.01) | |

(52) U.S. Cl.
CPC .......... *A61K 31/381* (2013.01); *A61K 31/137* (2013.01); *A61K 31/341* (2013.01); *C07C 251/24* (2013.01); *C07C 251/26* (2013.01); *C07D 307/52* (2013.01); *C07D 333/22* (2013.01)

(58) Field of Classification Search
CPC .................................................... C07C 251/24
USPC ........................................................ 514/448
See application file for complete search history.

(56) References Cited

U.S. PATENT DOCUMENTS

2009/0163545 A1* 6/2009 Goldfarb .............. A61K 31/122
514/312

FOREIGN PATENT DOCUMENTS

WO WO 2009/143141 A1 11/2009

OTHER PUBLICATIONS

Almazroa, Sarah et al., "Studies with Enaminones: The reaction of enaminones with Aminoheterocycles. A route to Azolopyrimidines, Azolopyridines and Quinolines," *Journal of Heterocyclic Chemistry*, 2004, 41(2):267-272.
El Turk, Farah et al., "An integrative in silico methodology for the identification of modulators of macrophage migration inhibitory factor (MIF) tautomerase activity," *Bioorganic & Medicinal Chemistry*, 2010, 18:5425-5440.
Kurbatov, V.P. et al., "Cobalt (II) Internal Complexes of Some 2-Aminovinyl Ketones," *Journal of General Chemistry USSR*, 1968, 38(10):2194-2197.
Zarzycka, Barbara et al., "Discovery of Small Molecule CD40-TRAF6 Inhibitors," *Journal of Chemical Information and Modeling*, 2015, 55:294-307.
Child, Ralph G. et al. (Apr. 1, 1977) "Fenbufen, a New Anti-Inflammatory Analgesic: Synthesis and Structure-Activity Relationships of Analogs," *Journal of Pharmaceutical Sciences* 66(4):466-476.

* cited by examiner

*Primary Examiner* — Nizal Chandrakumar
(74) *Attorney, Agent, or Firm* — Saliwanchik, Lloyd & Eisenschenk

(57) ABSTRACT

The present invention relates to compounds acting as selective inhibitors of CD40-TRAF6 interaction, their use as medicaments and their use in the treatment of (chronic) inflammatory diseases. The present invention also relates to pharmaceutical compositions comprising these compounds.

7 Claims, 23 Drawing Sheets

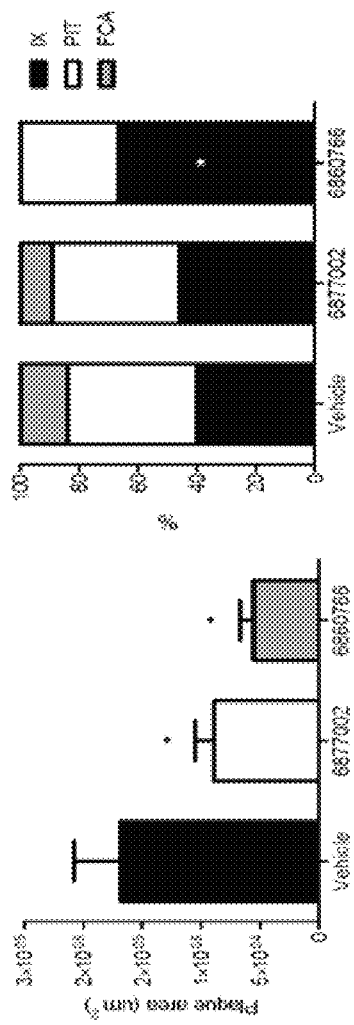
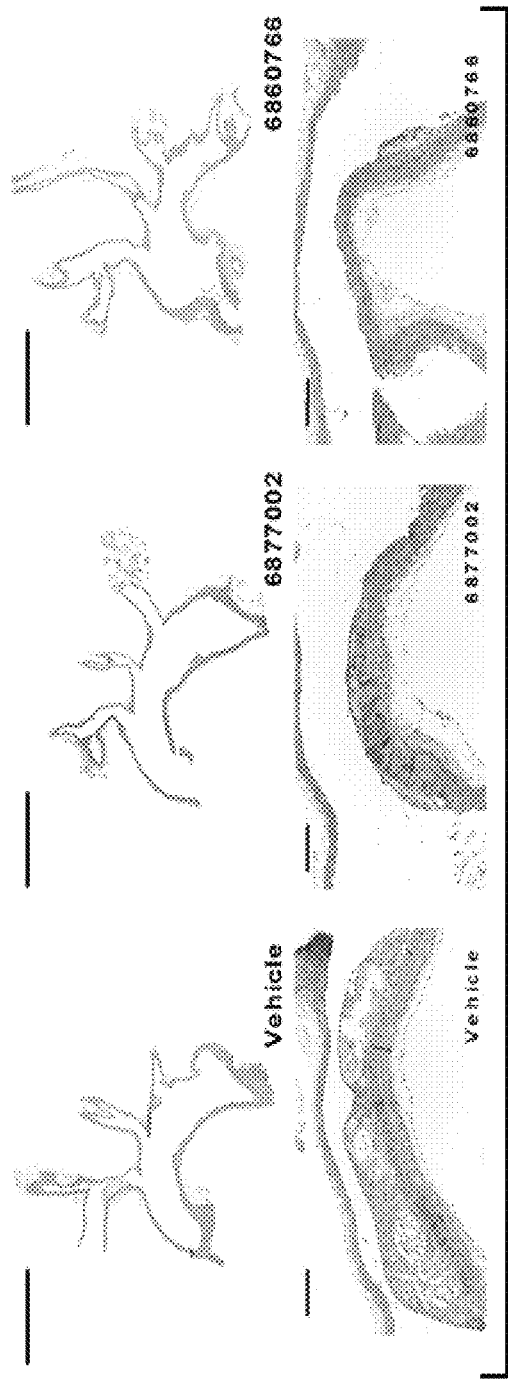
FIG. 7A  FIG. 7B  FIG. 7C

INHIBITORS OF CD40-TRAF6 INTERACTION

CROSS REFERENCE TO A RELATED APPLICATION

This application is a divisional application of co-pending application Ser. No. 14/417,708, filed Jan. 27, 2015; which is a National Stage Application of International Application Number PCT/EP2013/067714, filed Aug. 27, 2013; which claims priority to European Application No. 12181862.9, filed Aug. 27, 2012; all of which are incorporated herein by reference in their entirety.

The present invention relates to compounds acting as selective inhibitors of CD40-TRAF6 interaction, their use as medicaments and their use in the treatment of (chronic) inflammatory diseases. The present invention also relates to pharmaceutical compositions comprising these compounds.

Atherosclerosis is a chronic inflammatory disease of the large arteries that progresses with age [1, 2]. Atherosclerosis is characterized by the accumulation of immune cells, lipids and calcified components in the arterial wall, the so-called atherosclerotic plaque. The disease remains clinically silent for many decades, but when the atherosclerotic plaque ruptures, a thrombus will form on the plaque surface and will encroach the lumen, resulting in (myocardial) infarction or stroke, depending on the vascular bed affected [3].

HMG-coA-reductase inhibitors (statins) reduce the burden of cardiovascular disease only by 25%, underscoring an urgent need for pharmaceutical targets suitable for new drug development. One class of targets involves the components of the immune system. Besides lipid lowering, modulation of the immune system has been shown to be a powerful mediator in the control of atherogenesis [1, 2].

The inventors have previously found that the CD40-CD40L dyad, one of the members of the TNF receptor family of co-stimulatory molecules, is crucial in the progression of atherosclerosis. Genetic inhibition of CD40(L) resulted in a strong decrease in atherosclerosis. Moreover, atherosclerotic plaques contained less inflammatory cells and more collagen [4]. This phenotype is the human equivalent of an atherosclerotic plaque that is not prone to plaque rupture. The reduction of atherosclerosis and the inflammatory-poor, collagen-rich plaque phenotype did occur even when treatment with an anti-CD40L antibody was performed after atherosclerotic plaques had developed [5].

Although inhibition of CD40(L) is an effective therapy to reduce plaque burden and to make plaques less prone to rupture, long time treatment, as it is needed in atherosclerosis, will induce side effects such as the occurrence of thrombo-embolic events or increased vulnerability to infections due to immune suppression. To circumvent these side effects, the inventors' research focused on unravelling the CD40-signaling pathway that is involved in atherosclerosis. CD40 has no intrinsic signaling, but signals via TNF-receptor associated factors (TRAF), TRAF1, 2, 3, 5 or 6 [6]. By generating genetically modified hyperlipidemic mice that are CD40 deficient, but have been given a CD40 transgene with a mutated CD40-TRAF2/3/5 (CD40-T2/3/5 mice), a mutated CD40-TRAF6 (CD40-T6 mice) or a CD40 transgene with the 2 mutations (CD40-T2/3/5/6 mice), the inventors were able to unravel which CD40-TRAF interaction was crucial in the development of atherosclerosis. They found that only CD40-TRAF6, but not CD40-TRAF2/3/5 interactions were crucial for the development of atherosclerosis [7]. In absence of CD40-TRAF6 interactions, only small atherosclerotic plaques developed and influx of immune cells into the vascular wall had decreased significantly. This was accompanied by a phenotypic switch in monocyte subtypes. Absence of CD40-TRAF6 interactions decreased the amount of pro-inflammatory $Ly6C^{high}$ monocytes, whereas the number of patrolling $Ly6C^{low}$ anti-inflammatory monocytes was increased. In depth analysis of the immune cell composition in blood and lymphoid organs revealed no immune-suppressive side effects [7]. These findings make the CD40-TRAF6 interaction an interesting target for the development of pharmacological agents to treat not only atherosclerosis, but also other chronic inflammatory diseases such as obesity, inflammatory bowel disease and arthritis.

Accordingly, it was an object of the present invention to identify novel compounds that selectively inhibit the CD40-TRAF6 interaction and are, thus, useful in the treatment of (chronic) inflammatory diseases.

The object of the present invention is solved by a compound having the formula

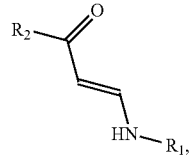

(I)
wherein
$R_1$ is a substituted or unsubstituted monocyclic aryl group; and
$R_2$ is a substituted or unsubstituted monocyclic aryl group or a substituted or unsubstituted monocyclic heteroaryl group;
or a pharmaceutically acceptable salt thereof
for use as a medicament.

The term "substituted", as used herein, means that at least one hydrogen atom attached to a member atom within a group is replaced with a substituent. Preferably, the substituents are independently selected from the group consisting of halogens (i.e., —Cl, —Br, —F and —I) and $C_1$-$C_3$-alkyl groups (i.e., methyl, ethyl, propyl). Particularly preferred substituents are selected from the group consisting of —Cl, —Br and —$CH_3$ (methyl).

The term "pharmaceutically acceptable salt", as used herein, means those salts of compounds of the invention that are safe and effective for use in mammals and that possess the desired biological activity.

In one embodiment, $R_2$ is selected from the group consisting of a substituted or unsubstituted phenyl group, a substituted or unsubstituted thiophenyl group and a substituted or unsubstituted furanyl group. In one embodiment, $R_2$ is selected from the group consisting of an unsubstituted phenyl group, an unsubstituted thiophenyl group and a substituted or unsubstituted furanyl group.

In one embodiment, $R_1$ is a substituted or unsubstituted phenyl group.

In one embodiment, said substituted phenyl group is a phenyl group substituted with one or more substituents independently selected from the group consisting of halogens (i.e., —Cl, —Br, —F and —I) and $C_1$-$C_3$-alkyl groups (i.e., methyl, ethyl, propyl). Preferably, said substituents are selected from the group consisting of —Cl, —Br and —$CH_3$ (methyl).

In one embodiment, $R_1$ is a mono- or disubstituted phenyl group.

In one embodiment, said phenyl group is substituted in the ortho- and/or para position. In one embodiment, said phenyl group is substituted only in the ortho- and/or para position (ortho position or para position or ortho and para position), i.e. it is not substituted in the meta position.

In one embodiment, said compound has a formula selected from the group consisting of

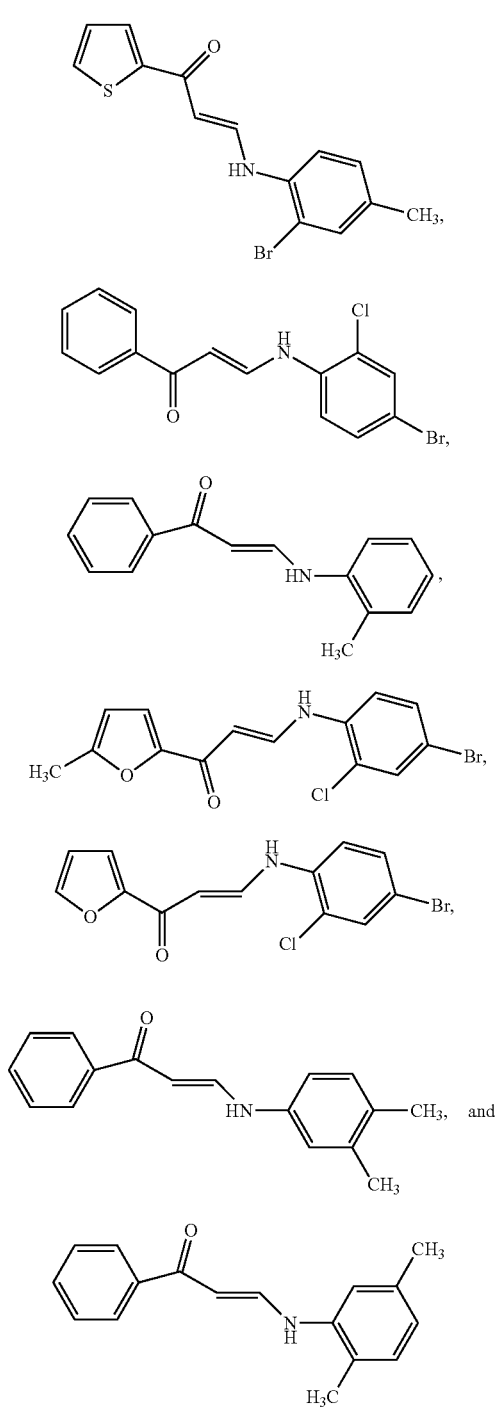

The object of the present invention is also solved by a compound as defined above or by a pharmaceutically acceptable salt thereof for use in the treatment of an inflammatory disease.

The object of the present invention is also solved by a compound as defined above or by a pharmaceutically acceptable salt thereof for use in the treatment of atherosclerosis.

The object of the present invention is also solved by a compound as defined above or by a pharmaceutically acceptable salt thereof for use in the treatment of obesity-associated adipose tissue inflammation, diabetes, insulin resistance, and/or hepatosteatosis.

The object of the present invention is also solved by a compound as defined above or by a pharmaceutically acceptable salt thereof for use in the manufacture of a medicament for the treatment of an inflammatory disease.

The object of the present invention is also solved by a pharmaceutical composition comprising a compound as defined above or a pharmaceutically acceptable salt thereof and at least one pharmaceutically acceptable carrier, diluent and/or excipient.

In one embodiment, said pharmaceutical composition comprises more than one compound as defined above or pharmaceutically acceptable salt thereof The object of the present invention is further solved by a method of treatment of an inflammatory disease, said method comprising the administration of an effective amount of a compound as defined above or of a pharmaceutically acceptable salt thereof or of a pharmaceutical composition as defined above to a person in need thereof Preferably, said inflammatory disease is a chronic inflammatory disease. Even more preferably, said inflammatory disease is selected from the group consisting of atherosclerosis, ischemic heart disease, myocarditis, inflammatory bowel disease, rheumatoid arthritis, multiple sclerosis, allergic encephalitis, psoriasis, atopic skin disease, osteoporosis, sepsis, peritonitis, hepatitis, obesity, obesity-associated adipose tissue inflammation, diabetes, insulin resistance, and/or hepatosteatosis In one embodiment, the term "atherosclerosis" is meant to include both early stages of atherosclerosis (intimal xanthoma and pathological intima thickening) and established atherosclerosis (fibrous cap atheromata, eroded and ruptured plaques). In one embodiment, said compound is intended to be used for the treatment of early atherosclerosis. In one embodiment, said compound is intended to be used for the treatment of established atherosclerosis.

The inventors of the present invention have successfully developed a unique set of compounds that block CD40-TRAF6 interactions. In contrast to, for example, antagonistic CD40 antibodies, these compounds specifically target the pro-inflammatory CD40-TRAF6 interaction, thereby preserving the function of CD40-TRAF2/3/5 in immunity.

The compounds strongly reduce inflammation, without causing immune-suppressive side effects. This finding is very significant, since most of the anti-inflammatory drugs on the market have immune-suppressive side effects. The compounds of the present invention were able to block disease development and progression in atherosclerosis, obesity, sepsis and peritonitis. The underlying mechanism in all diseases was a reduction in immune cell influx, especially monocytes, as well as a reduction in immune cell activation (especially macrophages).

Reference is now made to the figures, wherein

Figure 6B:
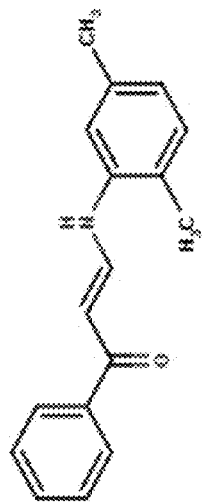
Figure 6A:
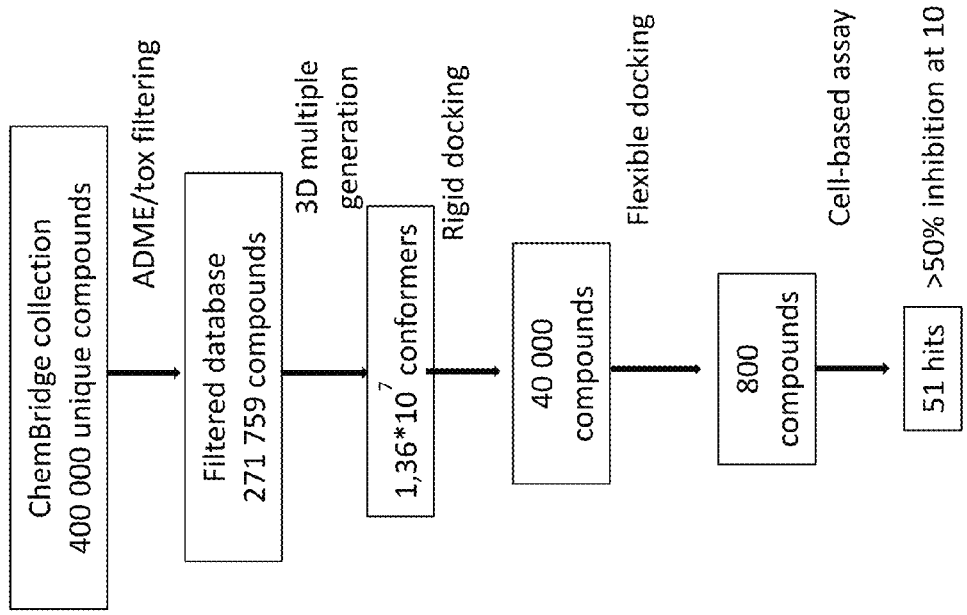
Figure 6C:
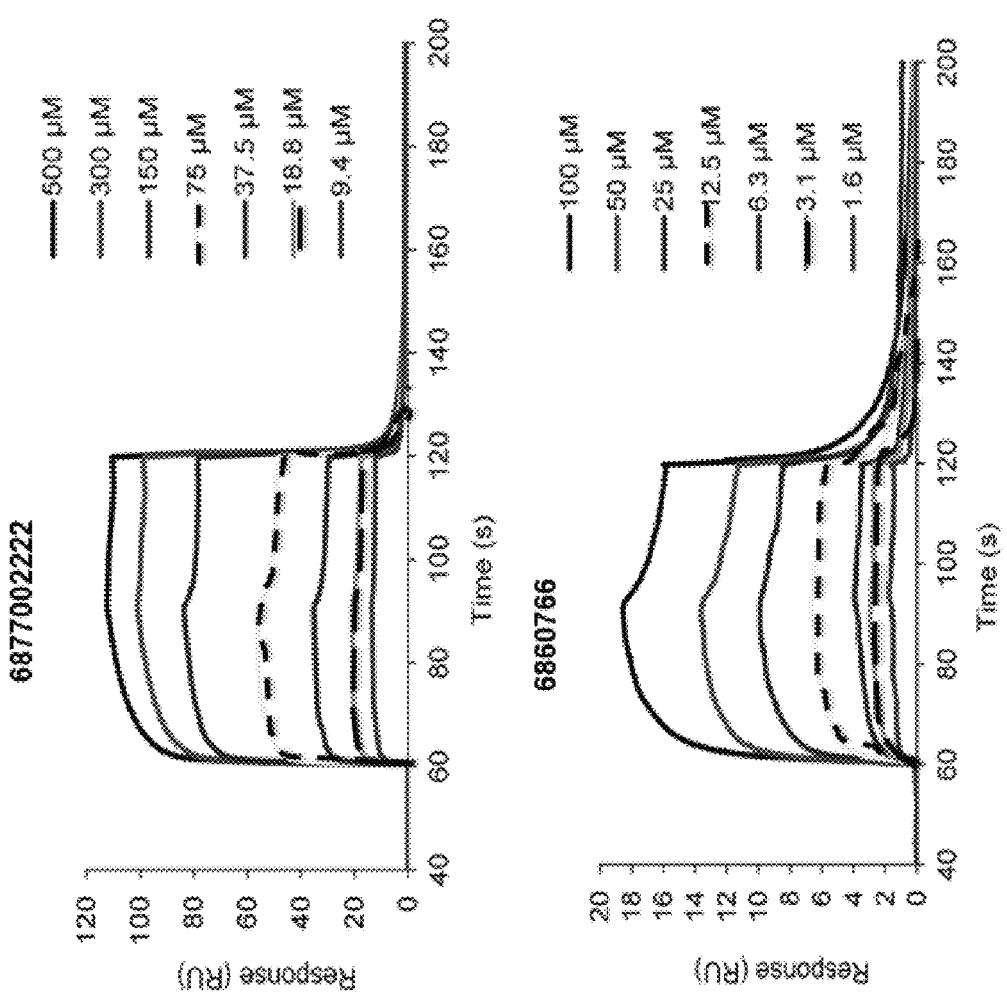

FIGS. 6A-6C Compound identification and characterization.

(6A) The VLS pipeline. The 400,000 compound collection was filtered based on absorption, distribution, metabolism, excretion, and toxicity (ADME/Tox) properties using 'Lipinski's rule of 5' which resulted in 271,759 compounds. Geometrical shape-fitting of structures, for each ligand all local energy minima in conformation space were calculated using a knowledge-based approach which resulted in 1.36× $10^7$ conformers. All 3D multi-conformers were submitted to the rigid docking protocol. The best-scoring 40,000 compounds were submitted to flexible docking. Subsequently, the top 800 compounds were submitted to the cell-based in vitro assay.

(6B) Compound 6877002.

(6C) SPR sensorgrams of compounds 6877002 and 6860766 binding to immobilized TRAF6 C-domain. Data represent three independent experiments.

FIGS. 7A-7G Compound treatment reduces atherosclerotic burden in $Apoe^{-/-}$ mice by limiting plaque inflammation.

(7A) Total plaque area in the aortic arch of 18 week old $Apoe^{-/-}$ mice is reduced by compound treatment (10 μmol/kg/day) for 6 weeks (n=15 for vehicle, n=14 for 6877002, n=12 for 6860766).

(7B) Atherosclerotic plaques were classified as described previously [3,7], pinpointing the early stages of the disease (intimal xanthoma and pathological intima thickening) and the advanced stages (fibrous cap atheroma). Compound 6860766 increased the incidence of initial lesions (intimal xanthoma (IX), pathological intimal thickening (PIT)) as it prevented the development of advanced lesions (fibrous cap atheroma (FCA)). (n=56 for vehicle, n=38 for 6877002, n=36 for 6860766).

(7C) Representative longitudinal images of the aortic arch and brachiocephalic trunk, stained with hematoxylin and eosin (HE). Compound treatment reduced plaque size and prevented the progression of initial lesions to more complex, advanced lesions. Scale bar: 2 mm (upper pictures) 100 μm (lower pictures).

(7D-7G) Compound-treatment reduced the number of leukocytes ($CD45^+$ cells) (D), macrophages/monocytes ($MAC3^+$) (F), T-cells (CD3) (E) and granulocytes ($Ly6G^+$) (G). All values represent mean±SEM. *, P<0.05.

Figure 8A:
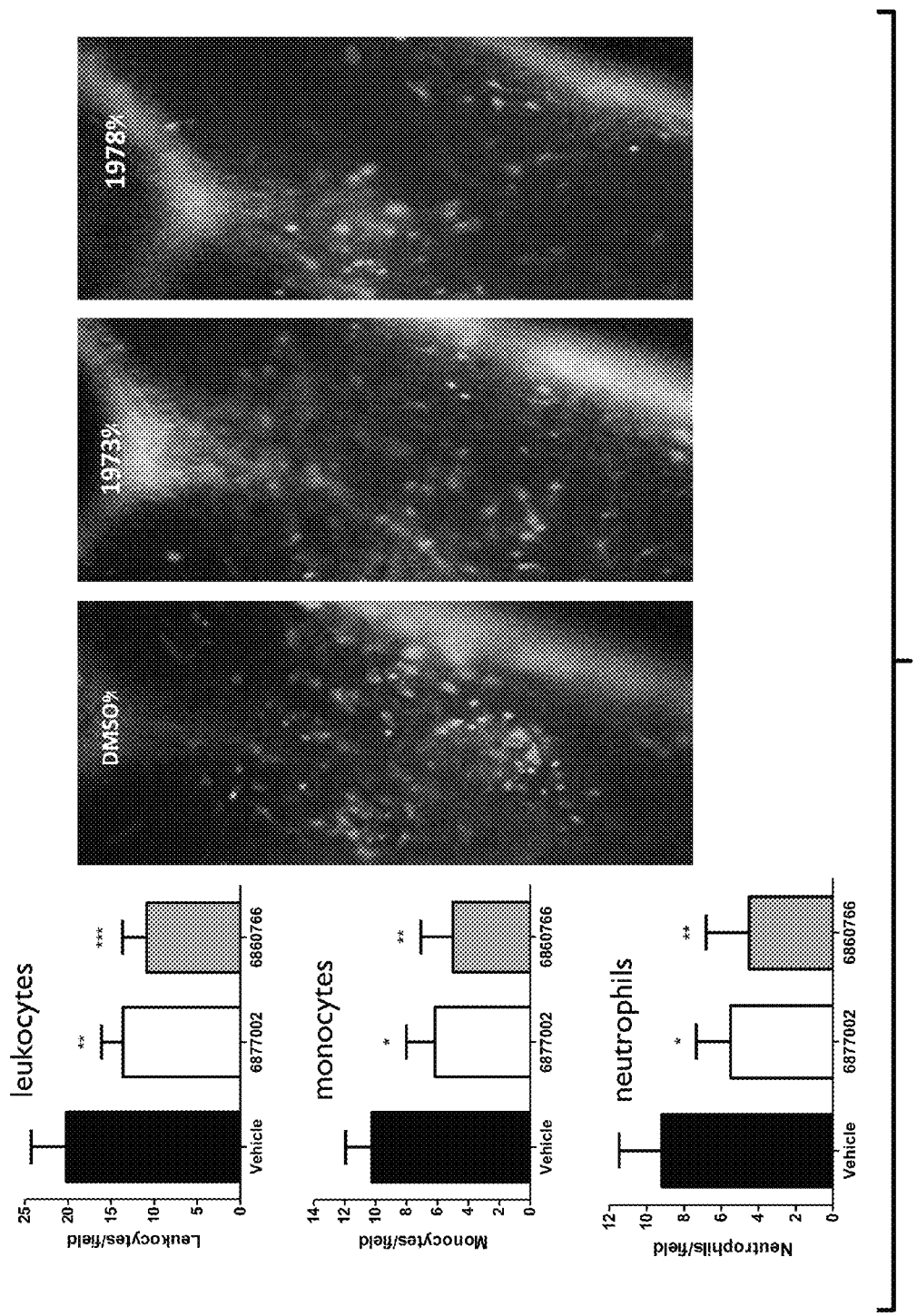
Figure 8B:
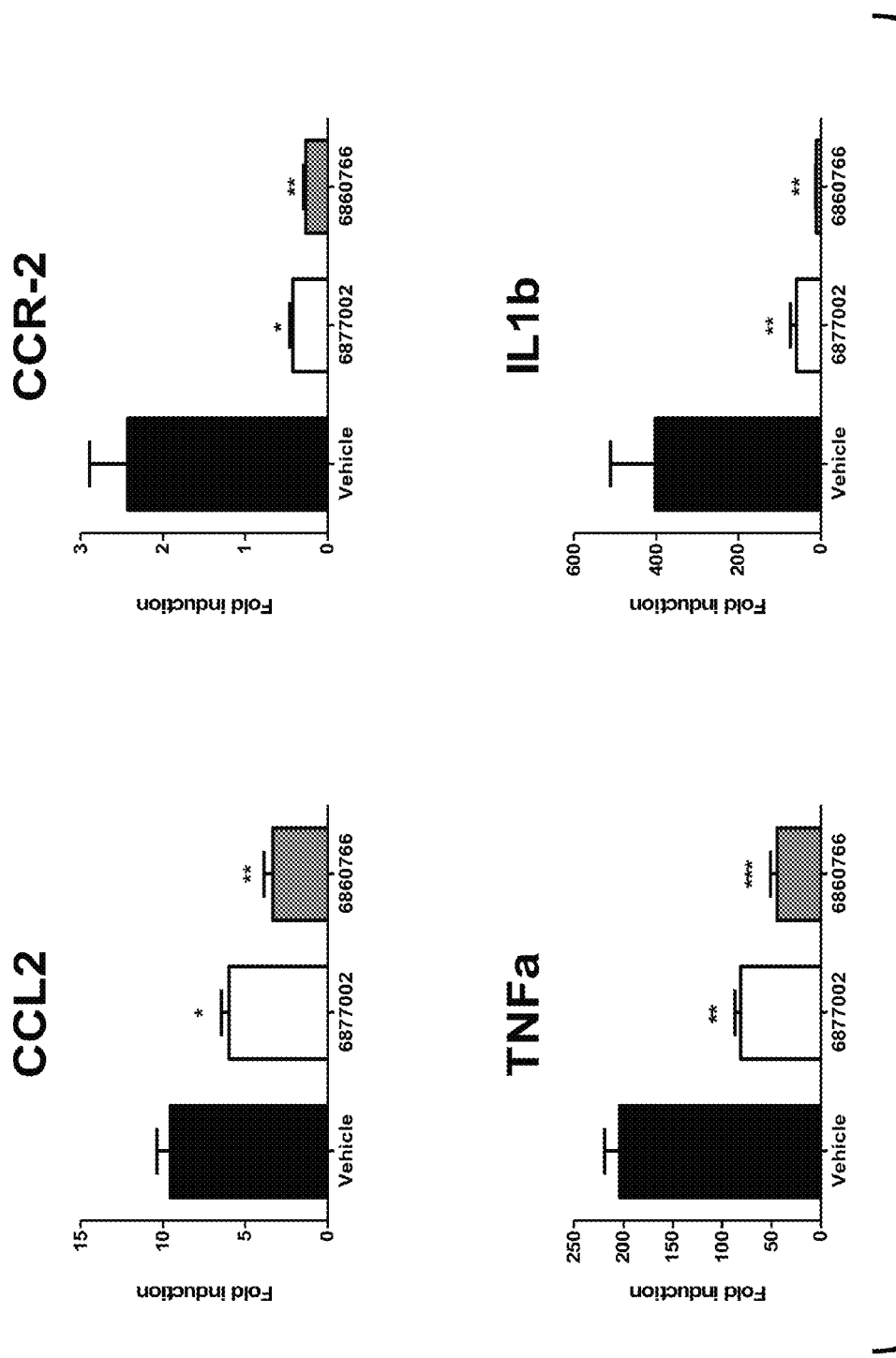
Figure 8B:
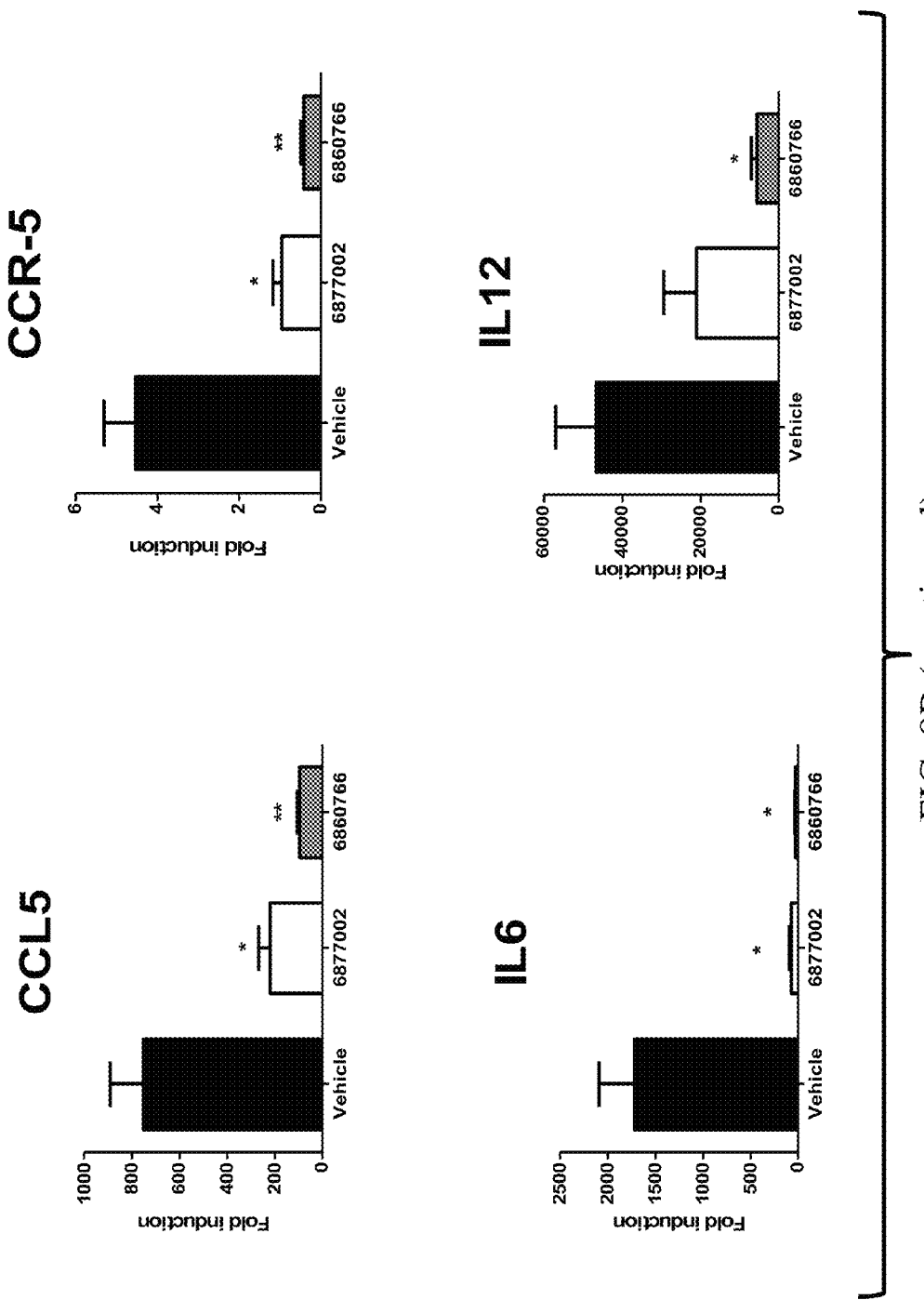
Figure 8B:
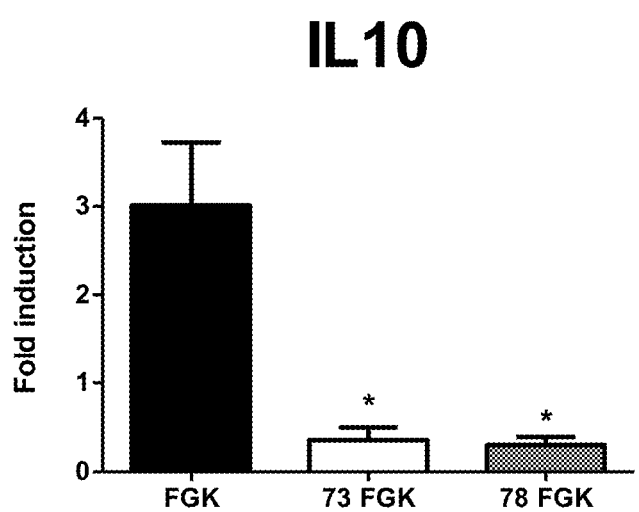

FIGS. 8A-8B Compound treatment impairs arterial myeloid cell adhesion and decreases chemokine and cytokine expression. Intravital microscopy of the carotid artery in Cx3cr1 egfp/wtApoe$^{-/-}$ mice fed a high fat diet for 6 weeks. To visualize neutrophils an antibody to Ly6G was instilled. After the initial recordings, leukocytes were stained by rhodamine 6G administration.

(8A) Leukocyte adhesion to the endothelium was reduced in 6877002-treated and 6860766-treated Apoe$^{-/-}$ mice. In particular, monocyte and granulocyte adhesion was impaired in treated mice (n=5-8 per group). Visualization of leukocyte adhesion to the carotid artery of Cx3cr1egfp/wtApoe$^{-/-}$ mice. In compound-treated mice, fewer rhodamine 6G-stained, and egfp and ly6G dots are observed, indicating that leukocyte adhesion (of both neutrophils and monocytes) to the artery wall is reduced.

(8B) The CD40-induced expression of the chemokine pairs CCL2, CCR2, CCL5, CCR5 in bone marrow-derived macrophages was impaired by the compounds. CD40-induced cytokine expression is prevented in compound treated bone marrow-derived macrophages. *, P<0.05; , P<0.01; * P<0.001.

Figure 9:
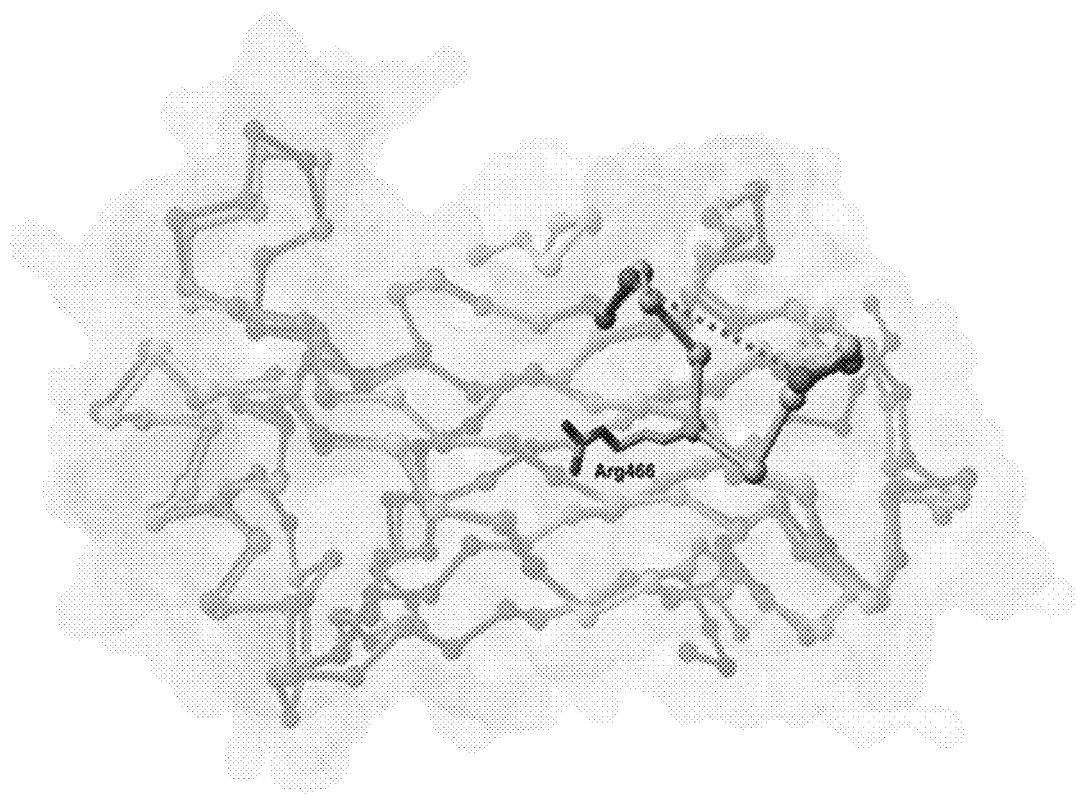

FIG. 9. Superimposition of x-ray structure of apo-structure and CD40-TRAF6 complex structure (dark grey and light grey, respectively).

Figure 10:
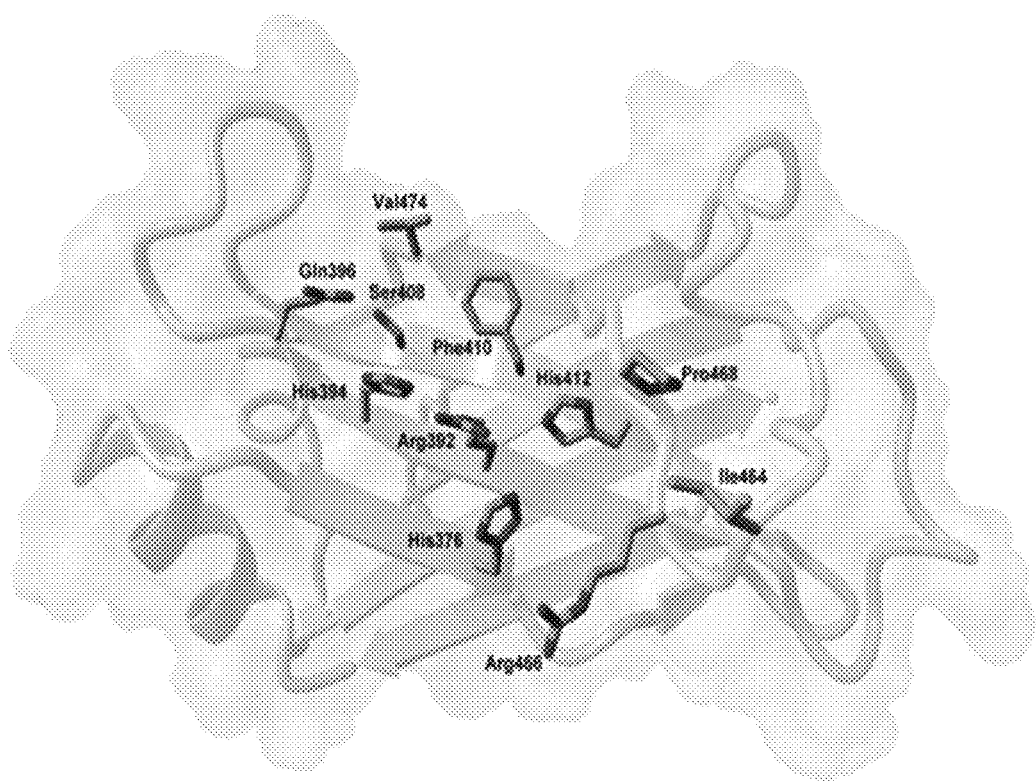

FIG. 10. Predicted druggable pocket. Residues which create pocket are depicted in cyan as follow: His376, Arg392, His394, Gln396, Ser408, Phe410, His412, Ile464, Arg466, Pro468, Gly470 and Val474.

Figure 11:
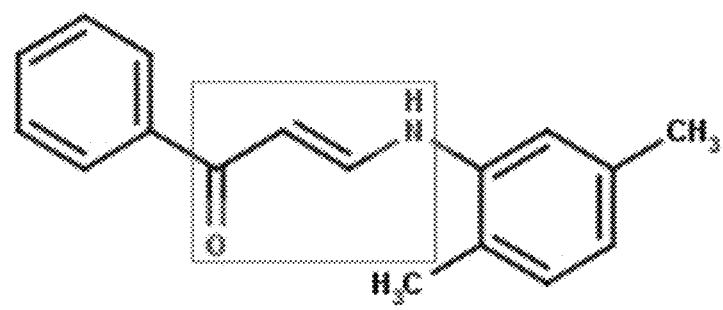

FIG. 11. The 19 compounds are characterized by two ring systems (R1 and R2) with different substitution groups connected by a common core, which consists of nitrogen, a double bond and oxygen.

Figure 12A:
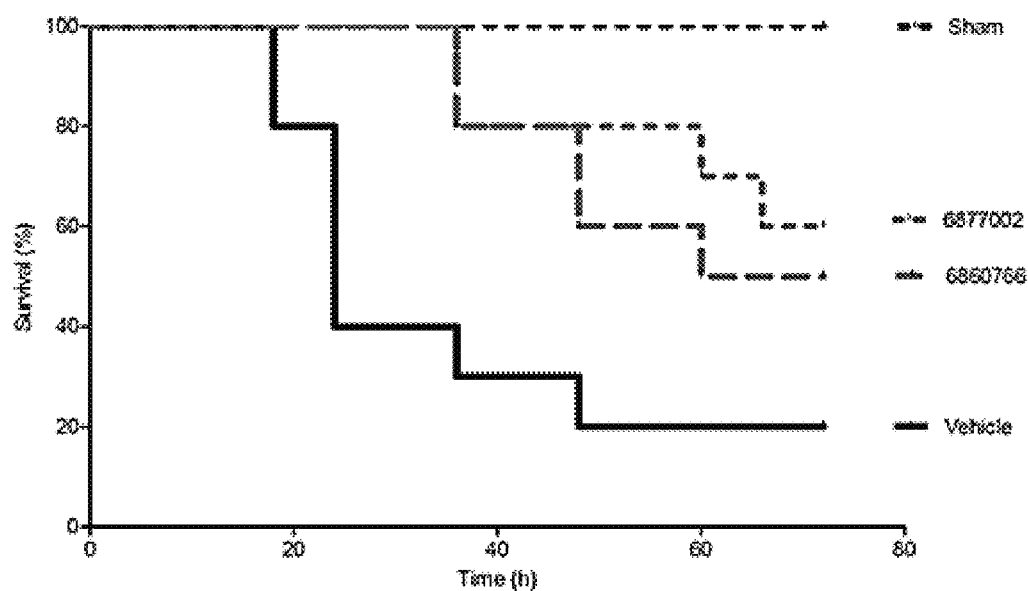
Figure 12B:
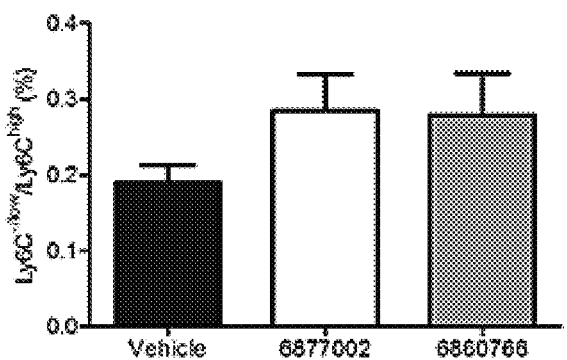

FIGS. 12A-12B. (12A) 6877002- and 6860766-treated mice subjected to cecal ligation and puncture exhibit increased survival rates, suggesting that the compounds did not induce systemic immunity during polymicrobial sepsis (n=10 per group). *, p<0.05; **, p<0.01. (12B) Compounds 6877002 and 6860766 increased the $Ly6C^{-/low}/Ly6C^{high}$ monocyte ratio in the peritoneum lavage of mice subjected to thioglycollate-induced peritonitis.

Figure 13B:
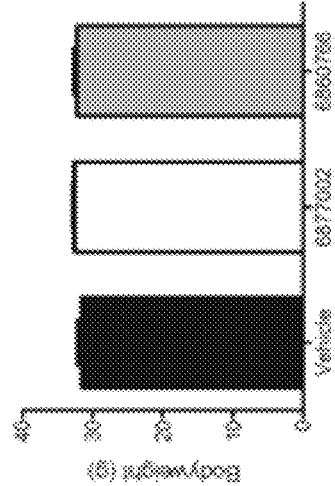
Figure 13A:
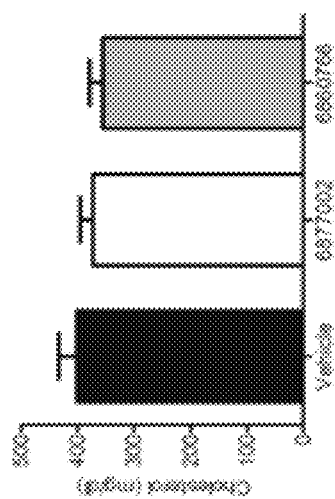
Figure 13C:
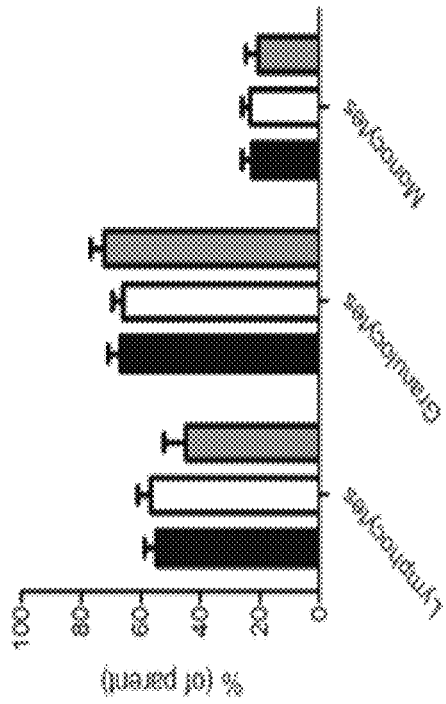

FIGS. 13A-13C. (13A-13B) Long-term (6 weeks) compound treatment did not affect bodyweight and plasma cholesterol levels in Apoe$^{-/-}$ mice. (13C) No differences in peripheral blood lymphocytes, granulocytes, and monocytes were observed.

FIGS. 14A-14D. CD40-TRAF6 interaction inhibitor improves metabolic dysregulation and AT inflammation WT male mice were fed a HFD for a total of 12 wks, receiving a CD40-TRAF6 interaction inhibitor (6877002) or control molecule starting at week 6 of feeding.

(14A) Body weight of HFD-fed inhibitor- or control-treated mice for 12 weeks.

(14B) Insulin tolerance test of HFD-fed inhibitor- or control-treated mice for 12 weeks.

(14C) SVF cells from gonadal adipose tissue of control- or inhibitor-treated mice was analyzed by FACS. CD45+ leukocytes and total macrophages or M1-macrophages (characterized as $CD11b^+F4/80^+$ and $F4/80^+CD11b^+CD11c^+$ respectively) are depicted.

(14D) Representative H&E pictures from liver of control- or inhibitor-treated mice. *p<0.05, for comparison with control treated mice. N=7-8 mice/group The present invention is now further described by means of the following examples, which are meant to illustrate, but not to limit the present invention.

EXAMPLES

Example 1

Virtual Ligand Screening

Figure 1:
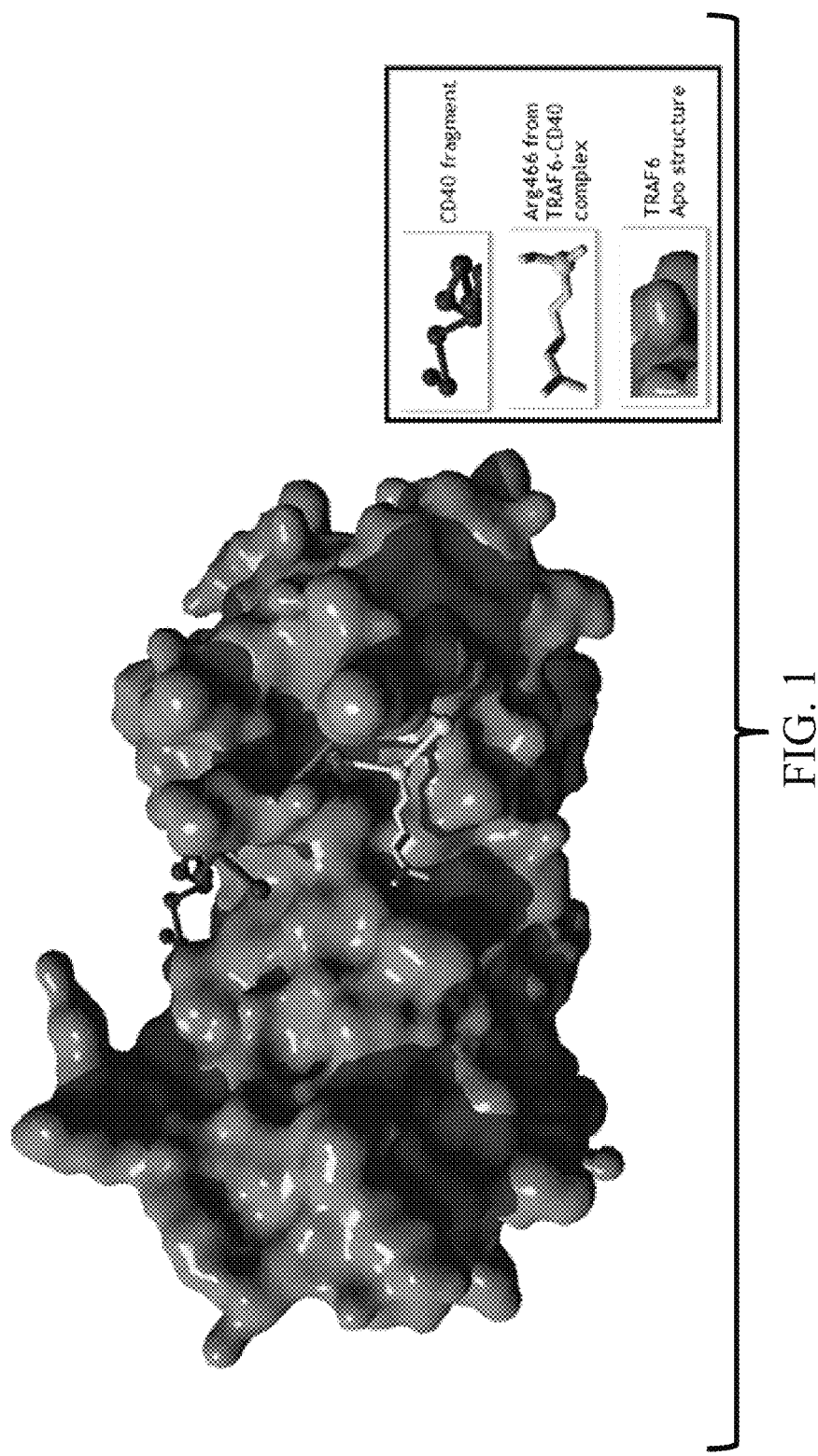
FIG. 1 shows the C-terminus of TRAF6 in complex with CD40 allowing the identification of a druggable pocket.

Genetic deficiency of CD40-TRAF6 interactions results in a strong decrease in atherosclerosis and a decreased influx of monocytes into the arterial wall by shifting the ratio between $Ly6C^{High}$ and $Ly6C^{low}$ monocytes. In order to develop a therapeutic agent that blocks CD40-TRAF6 interactions, the inventors modelled compounds that bind at the CD40-TRAF interface using three different structures of the C-terminal domain of Traf6 in complex with CD40 from the pdb protein database. By manual investigation of the protein, a druggable pocket was identified, and used as a starting point for virtual ligand screening (FIG. 1).

In the chembridge small molecule library (800,000 compounds), the inventors first performed an ADME/tox filtering (absorption, distribution, metabolism and excretion as well as toxicity) to find a drug candidate with desired pharmacokinetic and pharmacodynamic behaviour. Compounds were also selected according to the Lipinski rule of 5 for orally active drugs (1. Cannot have more than 5 hydrogen bond donors; 2. Cannot have more than 10 hydrogen bond acceptors; 3. Molecular weight has to be lower than 500 Daltons; 4. An octanol-water coefficient has to be lower than 5; and 5. The number of rotatable bonds has to be smaller than 10). After performing rigid and flexible docking analyses, 800 compounds had the potential to block the CD40-TRAF6 pathway in a biological system.

Validation of the Virtual Ligand Screening

The 800 compounds obtained from the virtual ligand screen were further tested in a cell culture system for their potential to block (CD40-induced) inflammation. Therefore, a macrophage cell-line containing an NFκB-luciferase was used. Macrophages were either stimulated with LPS or FGK45, a clustering antibody for CD40, to induce NFκB activation, an equivalent for inflammation. Of the 800 compounds, 48 compounds were able to reduce inflammatory activity by more than 50%.

Figure 2A:
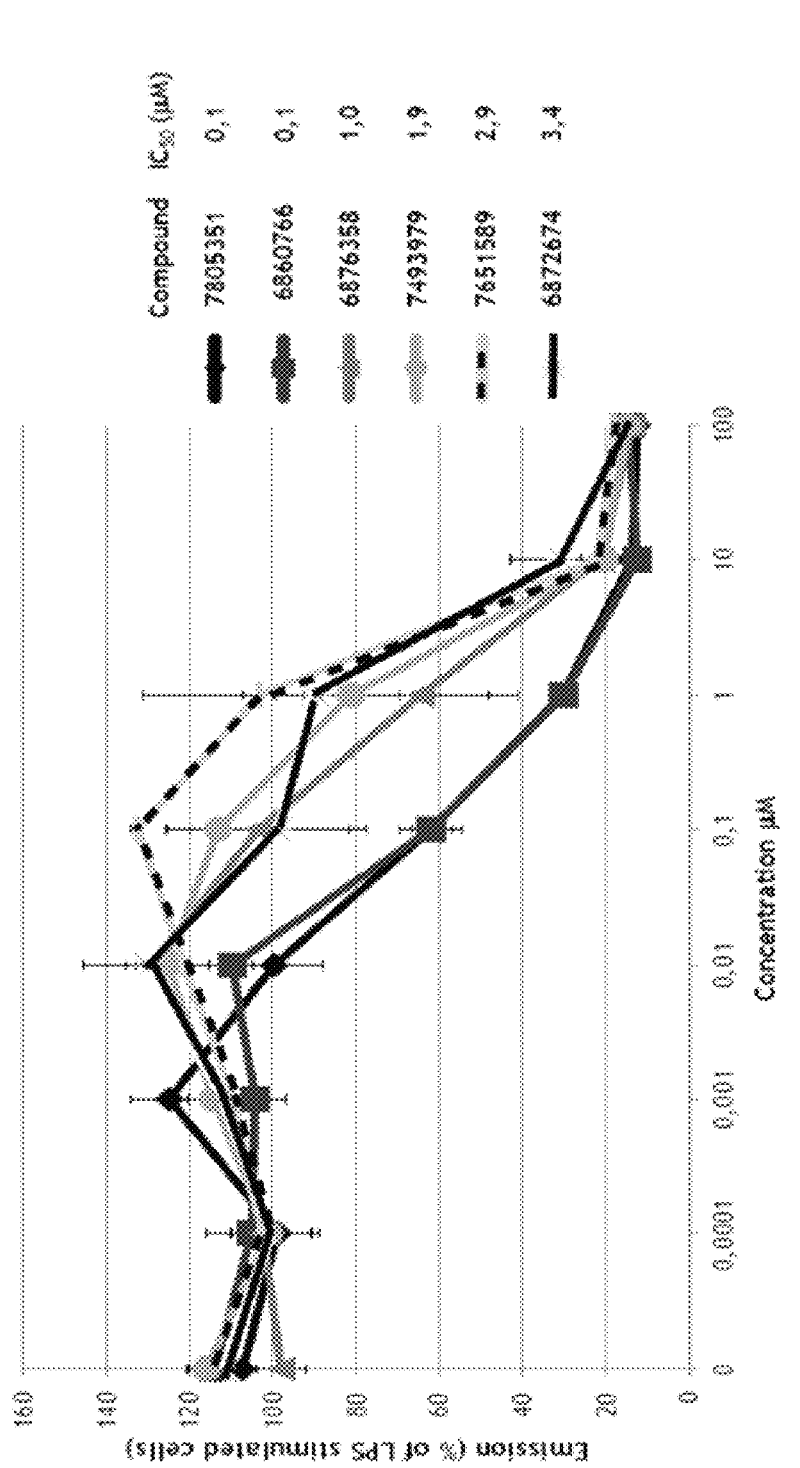
FIG. 2A shows the results of a cell culture assay revealing the ability of six exemplary compounds to reduce NFκB-activity.
Figure 2B:
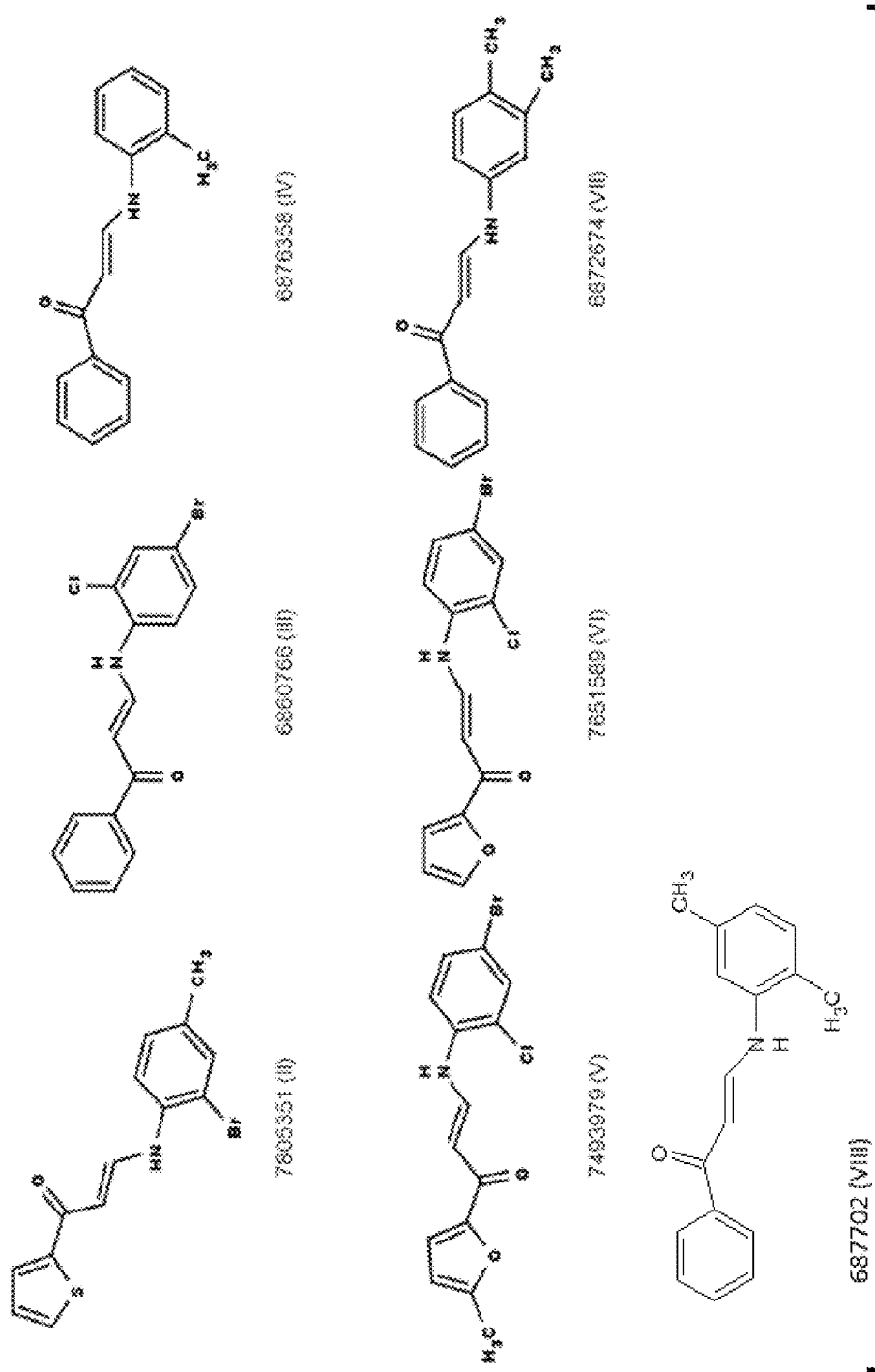
FIG. 2B shows the structures of seven exemplary compounds.

Based on their structure, these 48 compounds were divided into subgroups, and 150 novel compounds were developed and screened. This screen showed that 6 compounds dose-dependently blocked CD40 and/or LPS induced inflammation with an IC50 ranging from 400-7000 nM (FIG. 2A, the first six compounds, and FIG. 2B).

Structure of Active Compounds

Figure 3:
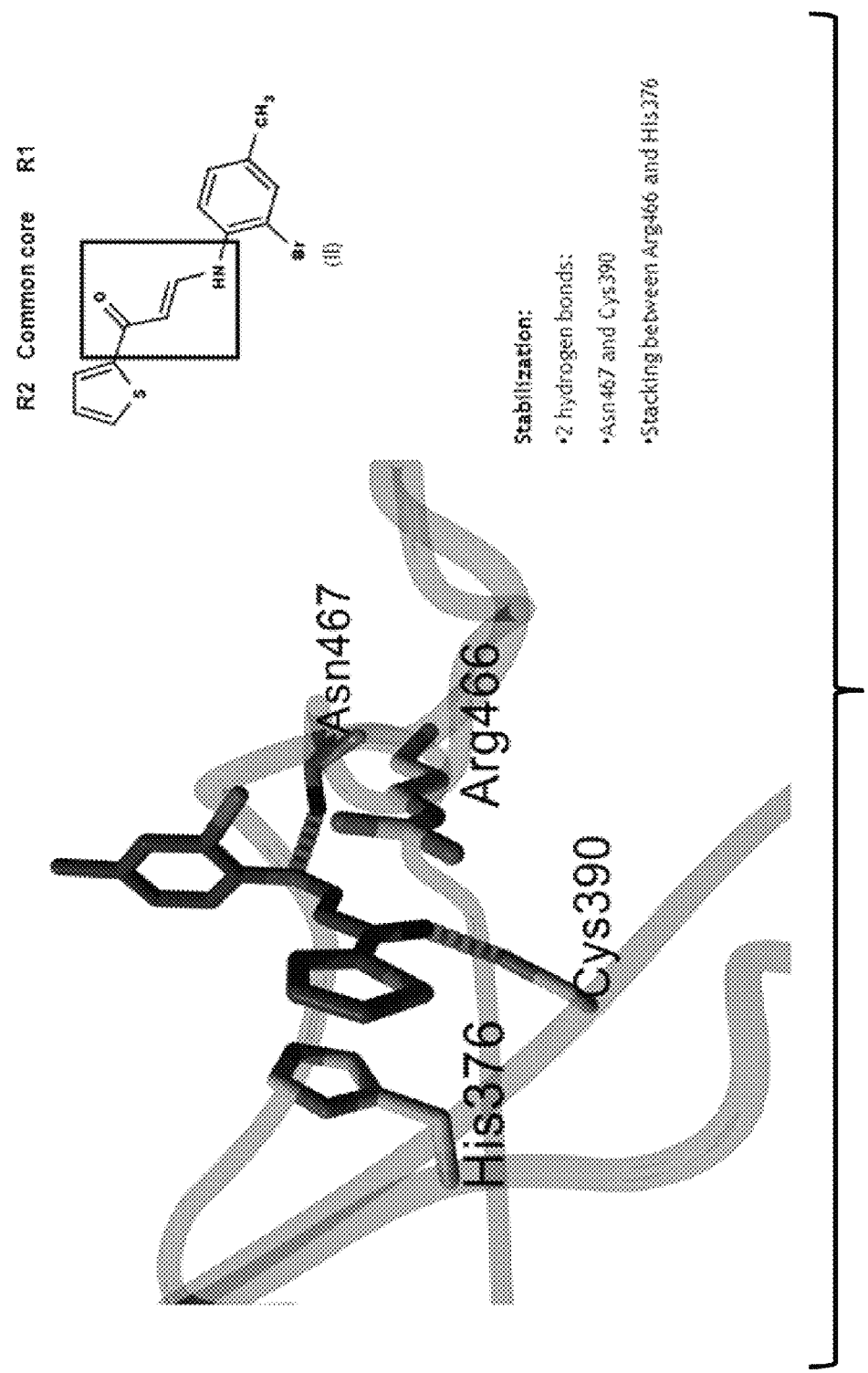
FIG. 3 shows the interactions of compound 7805351 (formula II) within the druggable pocket as well as the key structure of active compounds comprising a common core and two variable rings.
Figure 4:
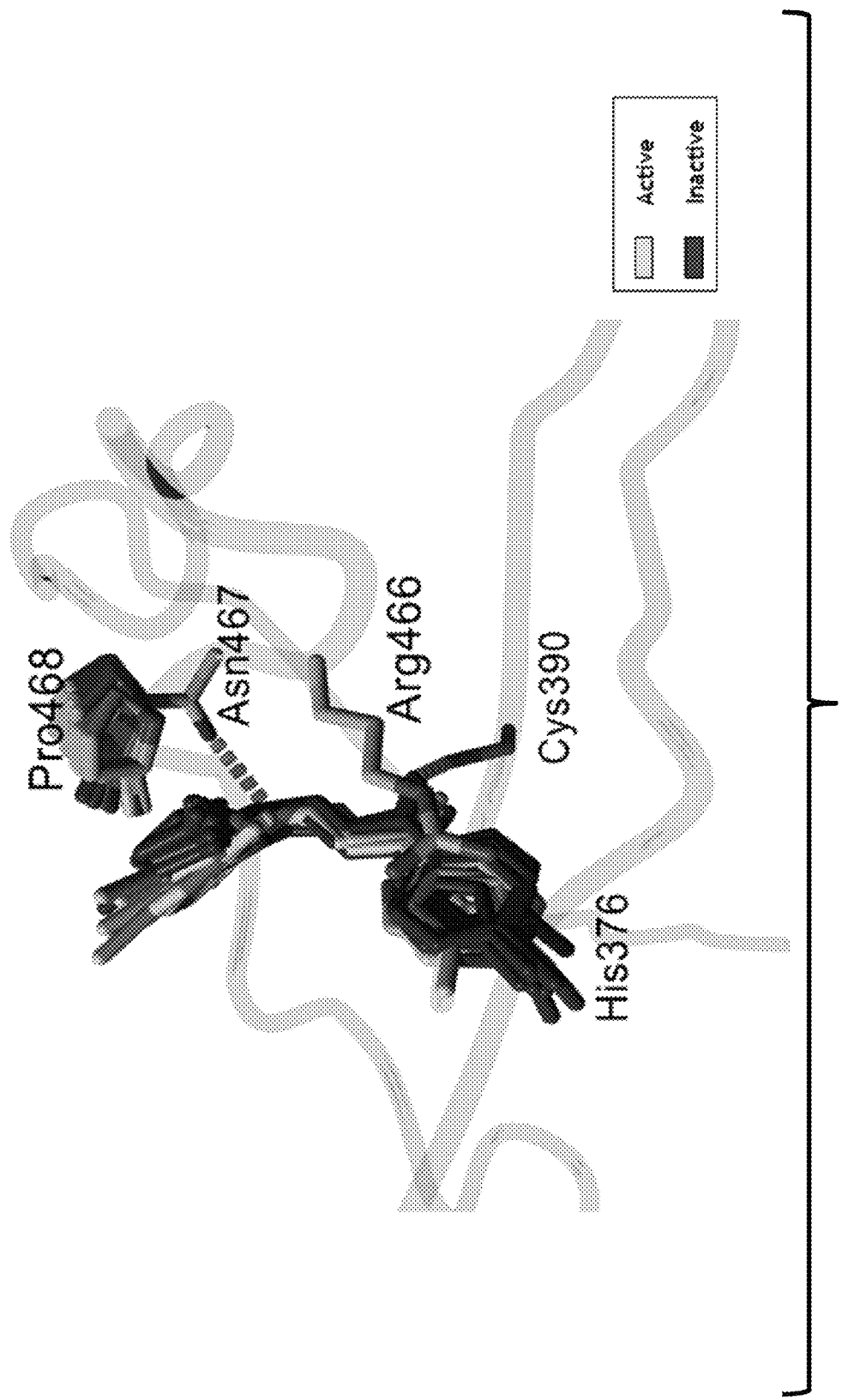
FIG. 4 shows a comparison of active and inactive compounds with regard to their positions within the druggable pocket.

The active compounds have a common linear core and two variable (hetero-) aryl groups ($R_1$ and $R_2$) (FIG. 3 and FIG. 11). Analysis of the virtual ligand screen and cell culture experiments revealed that modifications of the $R_1$ group that do not cause rearrangement of Pro468 of TRAF6 successfully block inflammation (FIG. 4). More than 90% of the active compounds have substitutions at the ortho or para position, whereas all the inactive compounds have substitutions at the meta position, causing steric hindrance.

In vivo Toxicology

The six active compounds that proved to efficiently block NFκB activity in cell culture were tested in a C57Bl6 mouse for any adverse side effects. The compound was injected daily at a concentration of 5 μM. The amount of leukocytes, as well as their subset distribution was investigated. No effects on total leukocyte counts were observed. However, the inventors observed a switch from the $Ly6C^{high}$ to the $Ly6C^{low}$ monocyte population, as was also true for the CD40-TRAF6 mouse model, thereby confirming the biological activity of the compound. No effects on B-cell, Dendritic cell or T-cell subsets were observed.

Inflammation Model

Figure 5:
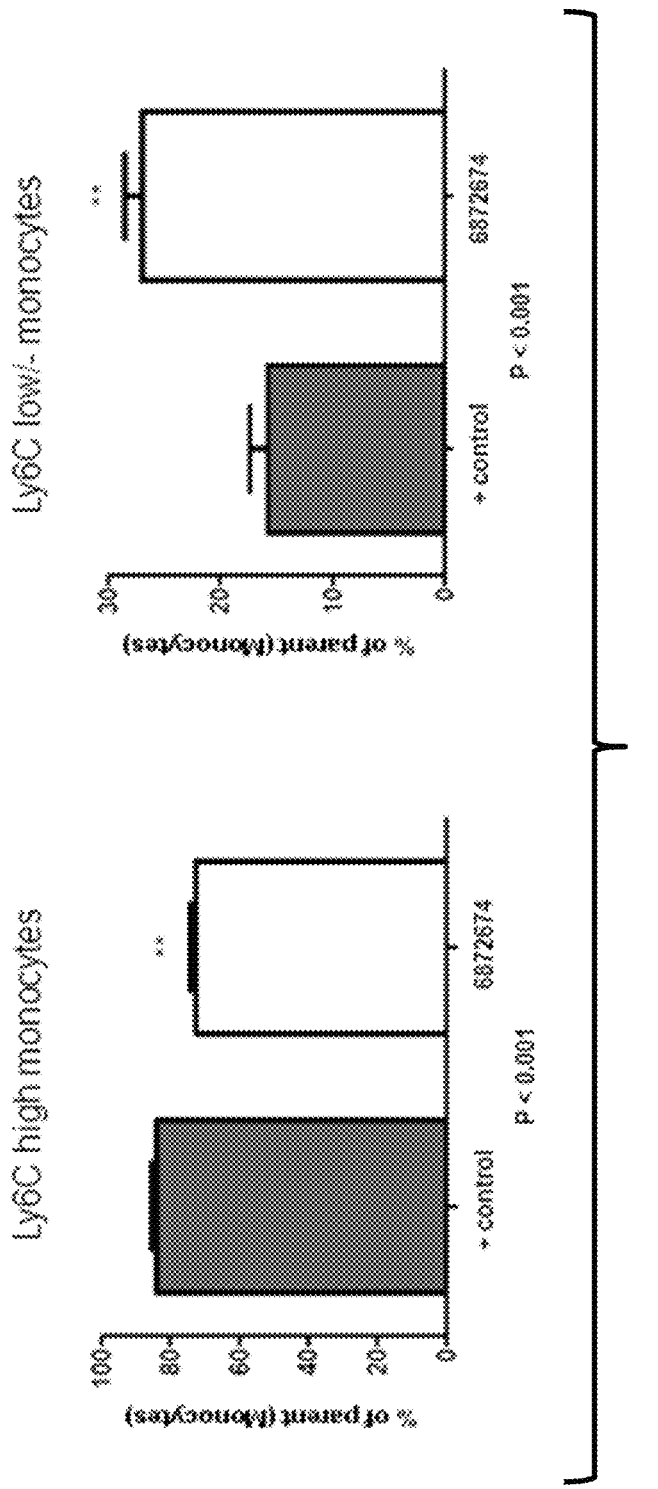
FIG. 5 shows the effect of one of the exemplary compounds in a mouse model of thioglycollate-induced peritonitis (=representative example for all of the compounds tested in vivo).

The six active compounds that proved to efficiently block NFκB activity in cell culture were tested in a mouse model of thioglycolate induced peritonitis. The compounds were injected intraperitoneally at a concentration of 5 μM, every 8 hours. After 18 hrs, the mice were sacrificed and peritoneal fluid, blood and spleen were analyzed for leukocyte number, monocyte, macrophage and DC subset distribution. Total leukocyte number was slightly elevated, but, as seen before in the CD40-TRAF6 mouse model and the toxicity study, the monocyte subset distribution switched towards the anti-inflammatory $Ly6C^{low}$ population (FIG. 5).

Example 2

Virtual Ligand Screening (VLS)

The crystal structure of a human CD40-TRAF6 complex (PDBid=1LB6) solved at resolution 1.80 Å, was used as a receptor template. Prior to its use in VLS, all solvent molecules, ions, and the co-crystallized CD40 peptide fragment were removed. Hydrogen atoms were added and their positions were optimized using the YASARA-WHATIF Twinset package. The TRAF6 apo-structure (PDBid=1LB4; solved at 2.40 Å) and the CD40-TRAF6 complex structure were aligned with the 3D superposition module implemented in the YASARA-WHATIF Twinset package. Based on analyses of the aforementioned 3D structural alignment, the side chain conformation of the Arg466 residue present in the CD40-TRAF6 complex structure (1LB6) was changed to represent the lowest energy rotamer. The new rotamer was retrieved from the YASARA backbone-dependent rotamer library. The programs ICM-PocketFinder and QSiteFinder were used to predict a druggable pocket in the TRAF6 template. The in silico small molecules collection from the Express Pick ChemBridge database (http://www.chembridge.com), version November 2009, was used as a starting point for the ligand selection process. This library of commercially available compounds consists of approximately 400,000 compounds. The compound collection was filtered using 'Lipinski's rule of five' as implemented in the ADME/Tox open-source FAF-Drugs2 program. Compounds with 1 Lipinski violation or with reactive groups were rejected. The OpenEye OMEGA conformer generation software was used to generate 3D multi-conformer structures for each of the small molecules and to add hydrogen atoms and Gasteiger partial charges. A hierarchical protocol that combines rigid and flexible docking methods, as described in [8, 9] was used. The FRED rigid-body docking program was used to dock the pre-generated multi-conformer library on the target structure. After the scoring of all TRAF6-compound complexes, the top 40,000 compounds were subjected to flexible docking and scoring by the Surflex program. A similarity search was performed on the ChemBridge database using the online search tool Hit2lead (http://www.hit2lead.com) to identify compounds with better inhibitory activity. Finally, fully flexible docking was performed with the Fleksy program. All molecular graphics in the associated article were produced with the YASARA-WHATIF Twinset package.

TRAF6 C-Domain Expression, Purification and Binding Analyses

His-tagged TRAF6 C-domain (residues 346-504) was expressed in E. coli using the pET21d expression vector (Novagen). Protein was purified via affinity chromatography, followed by gel filtration in running buffer (25 mM TRIS, 200 mM NaCl and 0.5 mM TCEP). The direct binding between the TRAF6 C-domain and the 6877002 and 6860766 compounds (for chemical structure see FIG. 6B and FIG. 2B, respectively) was measured via SPR (Biacore T200, GE Healthcare). TRAF6 C-domain was immobilized on Sensor Chip CM5 using the amine coupling method. This reached a density of approximately 12,000 and 7,500 RU. Compounds were dissolved in PBS buffer with 5% DMSO. All measurements were carried out at 25° C. and with a flow rate of 50 ul min⁻¹ in SPR running buffer (PBS, 0.05% Tween20, 5% DMSO, pH=7.4). Sensorgrams were corrected by subtracting the initial level of SPR signal before injection of the compounds or the TRAF6 C-domain. Data were analyzed using the BIAevaluation software. Equilibrium dissociation constants (Kd) were determined from a model of the steady state affinity (3 independent runs were averaged) (FIG. 6C).

In vitro Screen

RAW 264.7 cells, stably transfected with the $3^x$-κB-luc plasmid, were incubated with the small molecules for 1 hour at the indicated concentrations. Subsequently, cells were activated using lipopolysaccharide from *E. coli* (Sigma-Aldrich), a method to rapidly induce CD40-expression on macrophages. After 2 hours, cells were lysed and substrate was added according to the manufacturer's protocol (Luc-screen system, Applied Biosystems). Emission was measured at 450 nm using the Wallac Victor II luminometer.

In vitro Macrophage Culture

Bone marrow (BM) cells were isolated from C57Bl6 mice and cultured in RPMI supplemented with 15% L929-conditioned medium to generate BM-derived macrophages. BM-derived macrophages were activated by the agonistic CD40 antibody FGK45 (25 ug/ml, Bioceros BV) for 6 hours.

Quantitative PCR

RNA was isolated from BM-derived macrophages and reverse transcribed using an iScript cDNA synthesis kit (Bio-Rad). Quantitative (q)PCR was performed with a SYBR Green PCR kit (Applied Biosystems) on a ViiA 7 real-time PCR system (Applied Biosystems).

Animals

Male C57Bl6 and Apoe$^{-/-}$ (C57Bl6 background) mice were purchased from Charles River or bred at the local animal facility (Maastricht University, Maastricht, The Netherlands; Amsterdam Medical Center, Amsterdam, The Netherlands; and Ludwig Maximilians University, Munich, Germany). Cx3cr1egfp/+Apoe−/− were bred at the LMU.

Toxicity Studies

For in vitro toxicity studies, RAW264.7 cells were incubated with the small molecules as described above. Cell viability was analyzed using the Casy Cell Counter according to the manufacturer's protocol (Roche Applied Science). For in vivo toxicity studies, male C57Bl6 mice received a daily intraperitoneal injection of the small molecules (10 μmol/kg) for either 7 days (C57Bl6 mice) or 6 weeks (apoE$^{-/-}$ mice; atherosclerosis study). At sacrifice, absolute peripheral blood counts were determined using a scil Vet abc Plus+ haematology analyzer (Scil Animal Care Company B.V.). For histological analysis, organs were fixed in paraformaldehyde (4%, overnight), sectioned at 4 and stained with hematoxylin and eosin.

Flow Cytometry

At sacrifice, blood was obtained from the heart in EDTA-coated syringes. Erythrocytes were lysed by incubation with a hypotonic buffer (8.4 g of $NH_4Cl$ and 0.84 g of $NaHCO_3$ per liter of distilled water). Non-specific antibody binding was prevented by pre-incubation with a Fc-receptor blocking antibody (eBioscience). Leukocytes were labelled with CD3-FITC (eBioscience), B220-V500 (eBioscience), CD11 b-PeCy7 (BD), Ly6G-PE (BD), and Ly6C-APC (Miltenyi Biotec). Cells were analyzed on a FACSCanto II flow cytometer (BD).

Peritonitis and Cecal Ligation and Puncture (CLP)

To induce peritonitis in C57Bl6 mice, 3 ml 4% thioglycollate (Sigma) in PBS was injected intraperitoneally (IP). The compounds were administered at 0, 6, 12, and 15 hours after peritonitis induction. At euthanasia (18 hours after the induction of peritonitis), blood was collected and peritoneal cells were isolated via peritoneal lavage. Leukocytes were labelled with antibodies and analyzed by flow cytometry, as indicated above. Sepsis was induced by cecal ligation and puncture. Mice were anesthetized with an IP injection of ketamine (125 mg/kg body weight; Sanofi-Cefa GmbH Düsseldorf, Germany) and xylazine (12.5 mg/kg body weight; Phoenix Scientific). The abdomen was opened by longitudinal midline incision. After identification, the cecum was filled with feces, ligated 1 cm behind the tip, punctured with a 22 gauge needle, followed by the pressing out of a small amount of feces. Fascia, abdominal musculature and skin were closed by running sutures. Sham mice underwent the same surgical procedure without ligation and puncture of the cecum. Mice were treated with either the compounds (10 μMol/kg) or the vehicle, during CLP and 12 hours after CLP via IP injection.

Atherosclerosis

Apoe$^{-/-}$ mice were IP injected with the compounds at 10 μmol/kg/day for 6 weeks, starting at the age of 12 weeks, and were fed a normal chow diet throughout the experiment. They were then sacrificed and the arterial tree was perfused. The aortic arch and its main branch points were excised, fixed overnight, and embedded in paraffin. Longitudinal sections of the aortic arch were analyzed for plaque extent and morphology. For phenotypic analysis, immunohistochemistry (IHC) was performed for CD3 (Dako), CD45 (BD), Mac-3 (BD) and α-SMA (Sigma-Aldrich). Sirius red staining was performed to detect collagen. Morphometric analyses were performed using the Las4.0 software (Leica). Plasma cholesterol levels were measured enzymatically (Roche), and organs were analyzed by haematoxylin and eosin staining.

Intravital Microscopy

Intravital microscopy of the carotid artery was performed in Cx3cr1egfp/+Apoe−/− mice for 6 weeks on 0.15% cholesterol diet. Mice received a single IP injection of the compound or vehicle. A PE-conjugated antibody to Ly6G (1A8, 1 μg) was instilled via a jugular vein catheter 5 minutes prior to recording. After recording of neutrophil and monocyte adhesion, rhodamine 6G was administered to visualize all adherent leukocytes. Intravital microscopy was performed using an Olympus BX51 microscope equipped with a beam splitter to enable synchronized dual-channel recording, a Hamamatsu 9100-02 EMCCD camera, and a 10× saline-immersion objective. Olympus cell software was used for image acquisition and analysis.

Statistical Analysis

Data are presented as mean±SEM. Data were analyzed by using either an unpaired Student's t test, a Bonferoni-corrected Student's t test, or an ANOVA as indicated, using the GraphPad Prism 5.0 software (GraphPad Software, Inc.). P-values<0.05 were considered significant.

Example 3

All methods mentioned in this example were carried out as described in Example 2.

Identification of Small Molecule Inhibitors

To identify drug-like molecules that inhibit the CD40-TRAF6 interaction, an in silico structure-based virtual ligand screening (VLS) approach was used. The interaction between CD40 and TRAF6 was analyzed using the human TRAF6 apo-structure (PDB ID: 1LB4) and the structure of the CD40-TRAF6 complex (PDB ID: 1LB6). These analyses revealed conformational changes in the TRAF6 peptide-binding groove upon binding of CD40. In this process, Arg466, which is located in the CD40 peptide-binding groove, seems to be most affected (FIG. 9). Various orientations of this side chain were therefore explored to identify a potential druggable pocket in the CD40-TRAF6 interaction site (FIG. 10). A multi-stage screening approach on the ChemBridge compound collection was utilized to identify inhibitors of this pocket (FIG. 6A). This screening cascade, consisting of rigid and flexible docking as well as in vitro analysis, reduced the number of compounds from 400,000 to 800 using computational approaches. The 800 top-scoring compounds in the flexible docking were analyzed in vitro, using a cell-based NFκB reporter gene assay. This resulted in the identification of 51 compounds that reduced NFκB activation in a mouse leukemic monocyte/macrophage cell line (RAW 264.7) by at least 50% at 10 μM.

The 6 compounds that most effectively reduced NFκB activation in the in vitro test were used as a query for a similarity search in the ChemBridge database, which resulted in 150 analogues. The in vitro screen of these compounds revealed six additional bioactive compounds with equal or improved cellular activity compared to the initial best compound 6877002 (FIG. 2B). Compound 6877002 and these 6 identified bioactive analogues (FIG. 2B) all showed dose-dependent inhibition of NFκB activation in RAW cells (FIG. 2A).

Example 4

All methods mentioned in this example were carried out as described in Example 2.
The Small Molecules Directly Bind to TRAF6
To elucidate the structure activity relationship (SAR) of the analogues of compound 6877002 a 3-dimensional TRAF6-compound interaction model was built using fully flexible docking of all bioactive hits containing the molecular scaffold of compound 6877002. These compounds all possess two ring systems (R1 and R2; FIG. 11) with different substituents and are connected by the same linker. Apparently the binding of this compound class to TRAF6 is stabilized by 2 hydrogen bonds with residues Asn467 and Cys390 and π-π stacking interactions of the R2 ring with Arg466 and His376 (FIG. 3). Cellular activity of these compounds appears to correlate with the presence of substituents at either the ortho or para position and the absence of a substituent at the meta position. Substituents at the meta position seem to clash with Pro468 (FIG. 4). Compound 6877002 and compound 6860766 are the most active and most soluble ortho and meta substituted compounds respectively. These two compounds were selected for further studies.

Surface plasmon resonance (SPR) experiments were performed with the two compounds to confirm their direct binding to TRAF6. The equilibrium dissociation constants (Kd) to the TRAF6 C-domain are 97 μM and 42 μM for compounds 6877002 and 6860766, respectively (FIG. 6C). This correlates well with the activities observed in the three cellular assays described above.

Example 5

All methods mentioned in this example were carried out as described in Example 2.
Compound Treatment does not Result in Immunosuppression
The two selected compounds showed no in vitro cytotoxicity, as assessed by viability assays. Hematological and histopathological analyses of 13 vital organs revealed no toxic or immunosuppressive side effects in short-term (1 week) and long-term (6 week) treated mice. Long-term antibody-mediated inhibition of CD40 is believed to compromise systemic immunity. To assess whether our compounds induce systemic immunosuppression, polymicrobial sepsis was induced in C57Bl6 mice by cecal ligation and puncture. The mice were then treated with compound 6877002 or 6860766 (10 μMol/kg at t=0 h. and t=12 h.). Survival rates were increased by 150% (6877002) and 200% (6860766) (FIG. 12A), indicating that treatment did not compromise systemic immunity. In another experiment, C57Bl6 mice were subjected to thioglycollate-induced peritonitis to determine the effects of the compounds on the acute inflammatory response in vivo. Treatment with the two compounds induced an anti-inflammatory peritoneal monocyte profile with an increased $Ly6C^{-/low}/Ly6C^{high}$ monocyte ratio (FIG. 12B). The combined results indicate that compound 6877002 and 6860766 can reduce inflammation without compromising systemic immunity.

Example 6

Figure 7E:
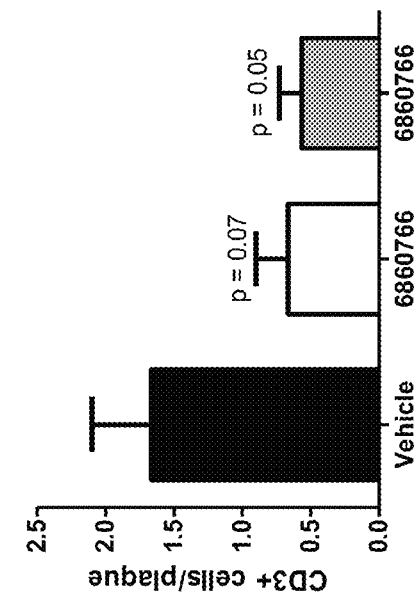
Figure 7G:
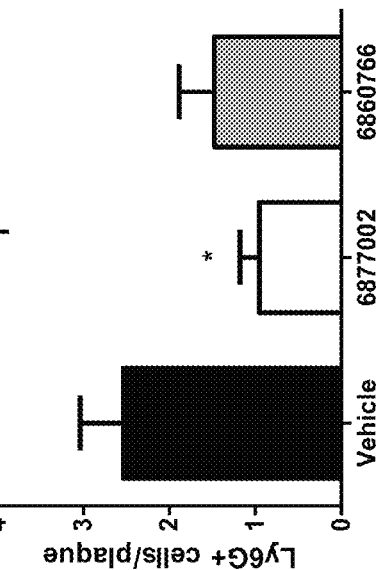
Figure 7D:
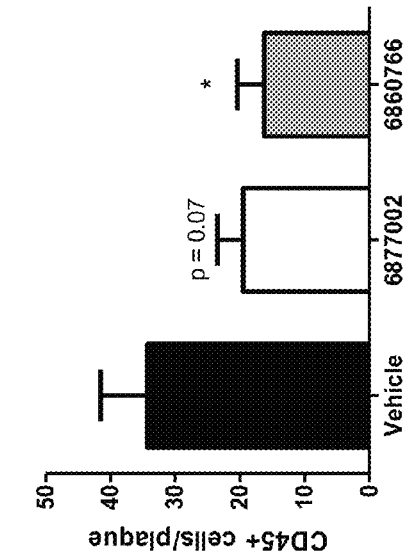
Figure 7F:
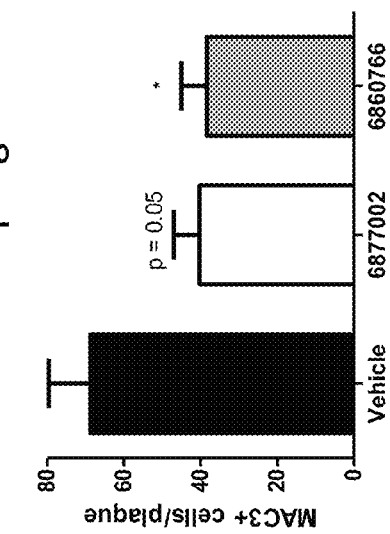

All methods mentioned in this example were carried out as described in Example 2.
Compound Treatment Reduces Atherosclerosis
To analyze the effects of these compounds on atherosclerosis, $Apoe^{-/-}$ mice were treated with compounds 6877002 or 6860766 at 10 μmol/kg/day for 6 weeks, starting at the age of 12 weeks. This did not affect body weight or plasma cholesterol levels (FIGS. 13 A and 13B). In addition, no differences in peripheral blood leukocyte counts or immune cell distribution were detected between compound-treated and vehicle-treated mice (FIG. 13C), indicating that long-term treatment with compound 6877002 and 6860766 did not cause leukocyte toxicity in vivo. 56 atherosclerotic lesions in the aortic arch of control-treated mice (n=15, mean 3.73 plaques/aorta), 38 lesions of 6877002-treated mice (n=14, mean 2.71 plaques/aorta), and 36 lesions of 6860766-treated mice (n=12, mean 3 plaques/aorta) were analyzed by histology. Compound treatment reduced total atherosclerotic plaque area per aortic arch by 47.1% (6877002) and 66.8% (6860766) compared to vehicle-treated mice (FIGS. 7A and 7C). Aortas from treated mice contained less advanced atherosclerotic lesions (fibrous cap atheromata), compared to controls (FIG. 7B). Correspondingly, the frequency of initial atherosclerotic lesions (intimal xanthoma and pathological intimal thickening) was increased (FIG. 7B), indicating that the progression of atherosclerosis was inhibited. Compound treatment reduced the number of leukocytes per plaque by 43.1% (6877002) and 52.6% (6860766) (FIG. 7D). Leukocyte subset analysis revealed that monocyte/macrophage ($Mac3^+$) (FIG. 7F), as well as granulocyte ($Ly6G^+$) (FIG. 7G) and T cell ($CD3^+$) (FIG. 7E) content had significantly decreased upon treatment with CD40-TRAF6 inhibiting compounds, For both compounds, no differences were observed in the number of apoptotic cells ($TUNEL^+$), smooth muscle cells ($αSMA^+$) and collagen (Sirius $Red^+$) content. Treatment with either of the two compounds thus prevents the progression of atherosclerosis in mice and induces a favorable atherosclerotic plaque phenotype that is low in inflammation.

Example 7

All methods mentioned in this example were carried out as described in Example 2.

Compound Treatment Impairs Leukocyte Recruitment to the Arterial Wall

To elucidate whether decreased plaque leukocyte numbers in compound-treated mice resulted from alterations in leukocyte recruitment to the endothelium, in vivo adhesion experiments were performed. Intravital microscopy demonstrated that the compounds reduced the recruitment of leukocytes, especially monocytes and granulocytes, to the arterial wall of Apoe$^{-/-}$ mice (FIG. 8A). Compound 6877002 and 6860766 reduced monocyte adhesion by 40.1% and 51.2% respectively (FIG. 8A), and neutrophil adhesion by 40.2% and 51.2% respectively (FIG. 8A).

Chemokines play a pivotal role in leukocyte recruitment. It was therefore analyzed whether the compounds affected chemokine expression. The compounds also inhibited the expression of the chemokine pairs CCL2-CCR2 and CCL5-CCR5 in bone marrow derived macrophages upon activation of CD40 signaling (FIG. 8B). Both chemokine pairs are known to promote myeloid cell accumulation within the arterial wall during atherogenesis.

Example 8

All methods mentioned in this example were carried out as described in Example 2.

Compound Treatment Improves the Inflammatory Phenotype of Macrophages

After adhesion to the activated endothelium, leukocytes critically contribute to the ongoing inflammation by secreting cytokines and reactive oxygen species. It was therefore analyzed whether compound treatment affected the expression of inflammatory mediators in bone marrow derived macrophages, because these account for the majority of leukocytes in atherosclerotic plaques. CD40-induced expression of TNFα, IL1β, IL6, IL10 and IL12 significantly decreased in both 6877002 and 6860766 treated macrophages (FIG. 8B). Treatment with the compounds also reduced the expression of iNOS by 67.7% and 80.6% for 6877002 and 6860766 respectively. These data demonstrate that compound treatment attenuates the inflammatory propensity of macrophages.

Example 9

Animals

C57Bl6 mice (Janvier, Saint Berthevin Cedex, France) were fed a high-fat diet for 12 wks, receiving compound 6877002 or control (10 µmol/kg/day) for 6 weeks i.p.

All mice were maintained under a 12 h light-dark cycle and were allowed free access to food and water. Food intake and body weight were measured weekly. After the experimental period, animals were euthanized, blood was collected and organs were dissected or stored at −80° C. for further analysis.

Biochemical Measurements and Glucose/Insulin Tolerance Test

An insulin tolerance test (ITT) was performed, and fasting insulin levels were measured. For the ITT, 5 h fasted mice were injected i.p. with insulin (0.75-2 mU/g, Actrapid, Novonordisk, Bagsvaerd, Denmark or Huminsulin, Lilly, Bad Homburg, Germany). Glucose levels were measured from whole blood using a glucometer (Roche Diagnostics, Basel, Switzerland) or a glucose meter device (Accu-Chek, Roche, Mannheim, Germany). Fasting insulin levels were measured in plasma by enzyme-linked immunosorbent assay (Mercodia, Uppsala, Sweden and Chrystal Chem Inc., IL, USA). Cholesterol levels were measured using a colorimetric assay (CHOD-PAP, Roche, Mannheim, Germany) and triglycerides by enzymatic assay (Wako, Neuss, Germany). Alternatively, triglycerides and cholesterol levels were monitored using the Accutrend Plus system (Roche, Mannheim, Germany), whereas liver triglyceride content was evaluated with a Triglyceride Quantification Kit (Abcam, Cambridge, UK).

Flow Cytometric Analysis

Stroma-vascular cells (SVC) were isolated from subcutaneous or gonadal AT (adipose tissue) using collagenase (Sigma-Aldrich, Zwijndrecht, The Netherlands or Invitrogen, Darmstadt, Germany). The samples were incubated at 37° C. with shaking until complete digestion, passed through a cell strainer (Falcon, distributed by BD biosciences, Breda, The Netherlands), washed and centrifuged to obtain the final SVC pellet. Spleens were washed after erythrocyte lysis. Fc-blocking (CD16/32 antibody) was performed prior to cell labeling. FACS for CD3, CD4, CD8, CD25, FoxP3, Ly6G, Ly6C, MHCII, B220, CD11c, CD11b, F4/80, CD206, CD44, CD45, CD62L, CD31 and CD19 was performed on SVC. All antibodies were purchased from e-Biosciences (San Diego, Calif., USA), BD Pharmingen (distributed by BD Biosciences), Miltenyi Biotec (Bergisch Gladbach, Germany) or BioLegend (Fell, Germany). Analyses were performed on a FACS Canto II (BD, Heidelberg, Germany), using FACSDiva 6.1.3 software.

Real Time PCR

Total RNA was extracted using Trizol (Invitrogen). cDNA was synthesized using i-Script cDNA synthesis kit (BIO-RAD). PCRs were performed with a Bio-Rad instrument and software under standard conditions. The relative amounts of the different mRNAs were quantified by using the second derivate maximum method. In other experiments, relative expression levels of each gene were quantified by using the SsoFast EvaGreen Supermix (BioRad). Results were expressed relative to the control group (vehicle treated mice)

Statistical Analysis

Results are indicated as means±SEM. Data were analyzed by a Student's T-Test or a Mann-Whitney U test. The ITT and body weight gain results were analyzed by a 2-way ANOVA. Significance was set at $P<0.05$.

Example 10

All methods mentioned in this example were carried out as described in Example 9.

Figure 14A:
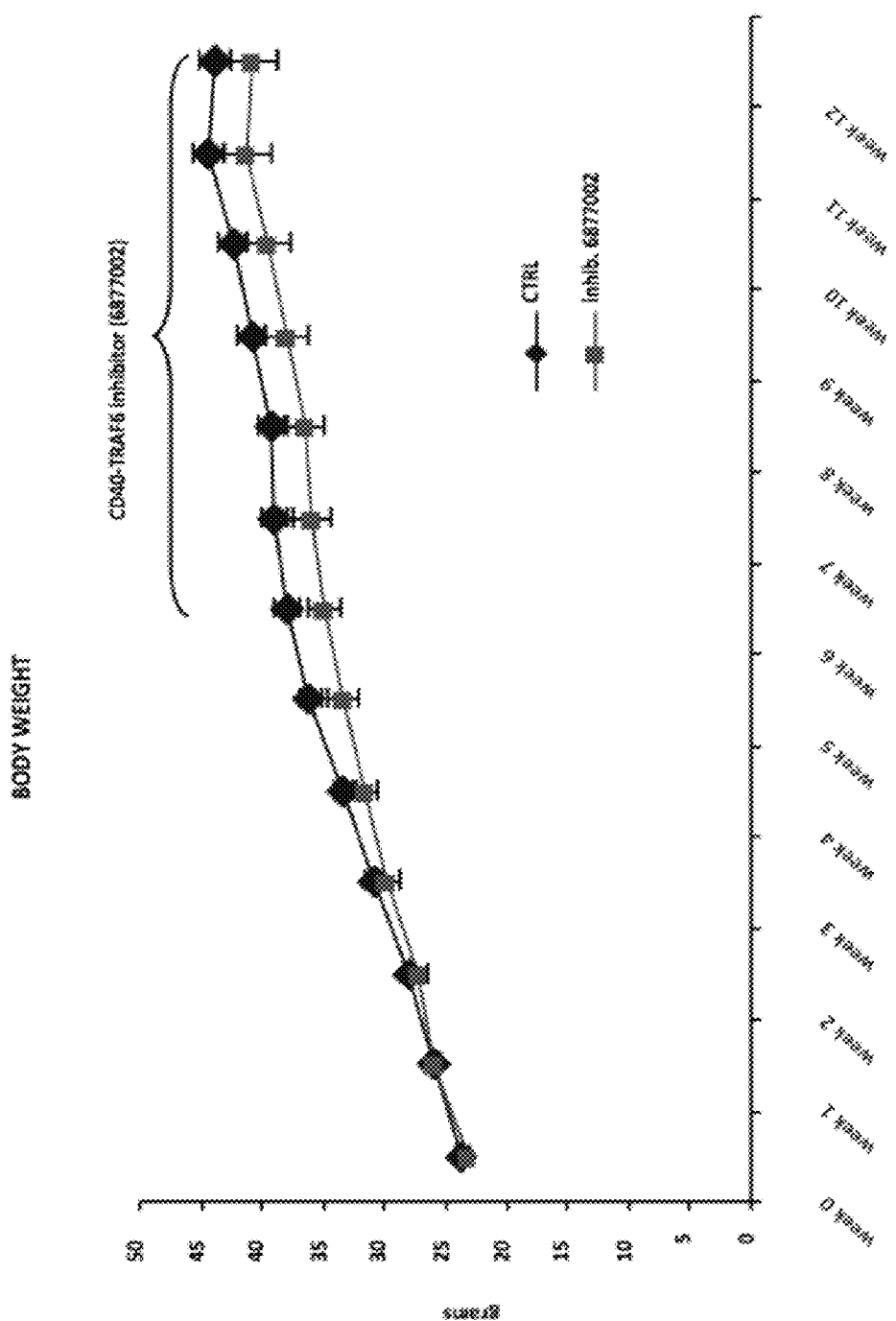
Figure 14B:
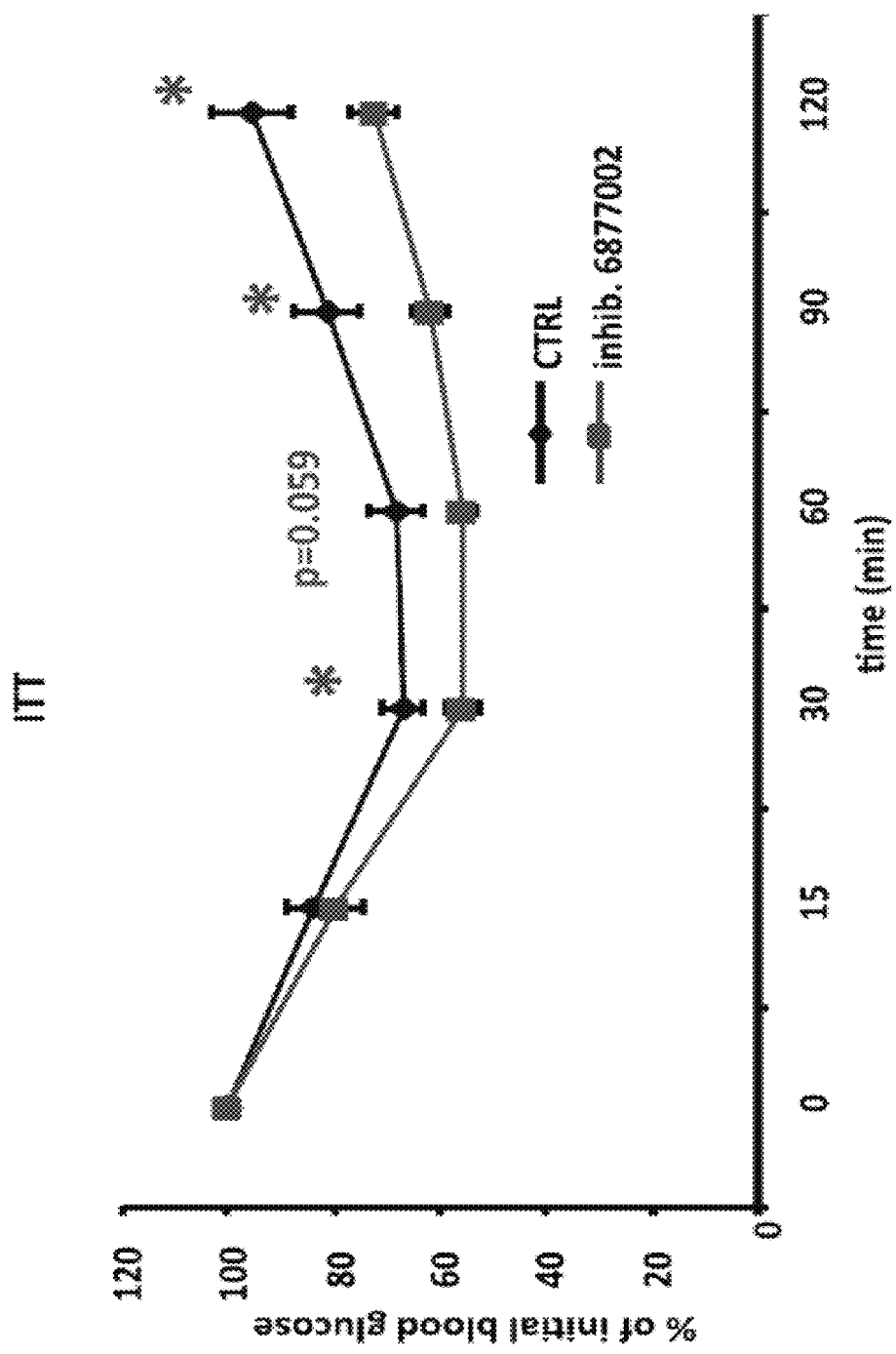
Figure 14C:
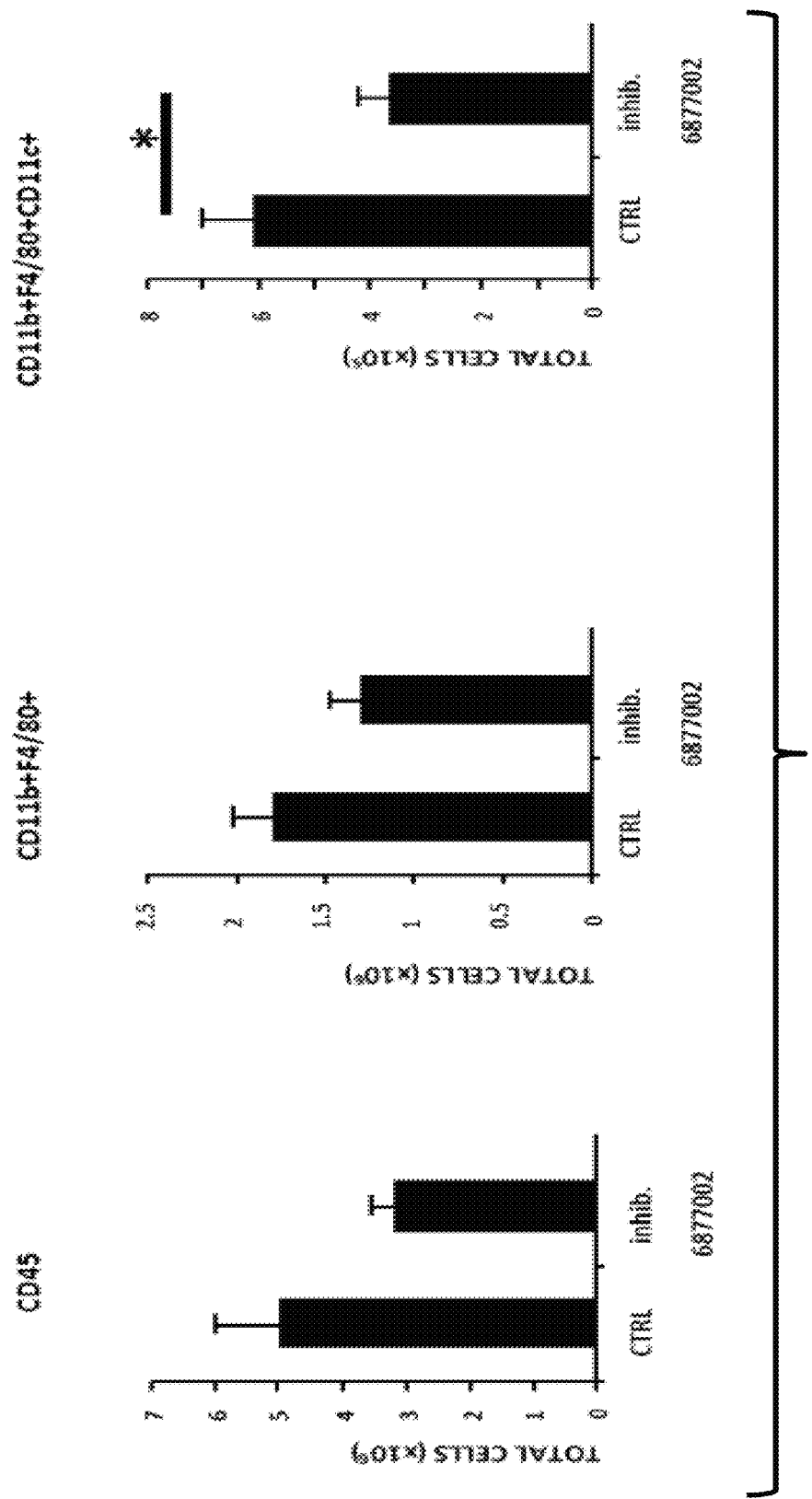
Figure 14D:
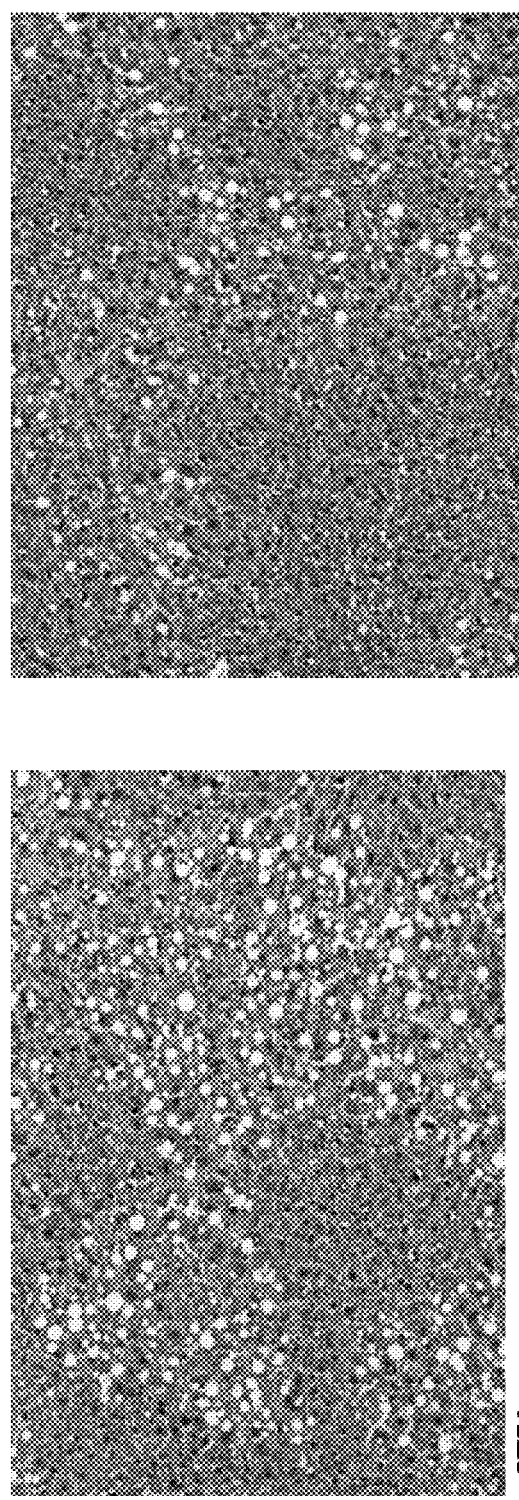

Pharmacologic Inhibition of the CD40-TRAF6 Pathway Ameliorated Obesity-related Metabolic Complications C57Bl6 mice were fed a HFD for 6 wks, and then received the small molecule inhibitor compound 6877002 (for structural formula see FIG. 6B), for another 6 wks. After this short treatment period, 6877002 treated mice did not show a change in weight, but already exhibited improved insulin sensitivity compared to the vehicle treated mice (FIGS. 14A, 14B). Moreover, gonAT (gonadal adipose tissue) inflammation was less severe after treatment with 6877002, with a remarkable reduction in macrophages and especially CD11b$^+$F4/80$^+$CD11c$^+$ (M1) macrophages (FIG. 14C). Interestingly, treatment with the CD40-TRAF6 inhibiting compound reduced liver steatosis (FIG. 14D). Thus, the compounds according to the present invention are effective in the treatment of obesity, especially for ameliorating metabolic complications like insulin resistance and steatosis, and for reducing macrophage and T-cell influx into the adipose tissue.

REFERENCES

[1] Weber C, Noels H. Atherosclerosis: current pathogenesis and therapeutic options. Nat Med 2011; 17: 1410-1422.
[2] Hansson G K, Hermansson A. The immune system in atherosclerosis. Nat Immunol. 2011; 12: 204-212.
[3] Virmani R, Kolodgie F D, Burke A P, Farb A, Schwartz S M. Lessons from sudden coronary death: a comprehensive morphological classification scheme for atherosclerotic lesions. *Arterioscl Thromb Vasc. Biol.* 2000; 20:1262-1275.
[4] Lutgens E, Gorelik L, Daemen M J, de Muinck E D, Grewal I S, Koteliansky V E, Flavell R A. Requirement for CD154 in the progression of atherosclerosis. *Nat Med.* 1999; 5:1313-1316.
[5] Lutgens E, Cleutjens K B, Heeneman S, Koteliansky V E, Burkly L C, Daemen M J. Both early and delayed anti-CD40L antibody treatment induces a stable plaque phenotype. *Proc Natl Acad Sci USA.* 2000; 97:7464-7469.
[6] Engel D, Seijkens T, Poggi M, Sanati M, Thevissen L, Beckers L, Wijnands E, Lievens D, Lutgens E. The immunobiology of CD154-CD40-TRAF interactions in atherosclerosis. *Semin Immunol.* 2009; 21:308-312.
[7] Lutgens E, Lievens D, Beckers L, Wijnands E, Soehnlein O, Zernecke A, Seijkens T, Engel D, Cleutjens J, Keller A M, Naik S H, Boon L, Oufella H A, Mallat Z, Ahonen C L, Noelle R J, de Winther M P, Daemen M J, Biessen E A, Weber C. Deficient CD40-TRAF6 signaling in leukocytes prevents atherosclerosis by skewing the immune response toward an antiinflammatory profile. *J Exp Med* 2010; 207:391-404.
[8] M. McGann, FRED pose prediction and virtual screening accuracy. *J. Chem. Inf. Model,* 51, 578-596 (2011).
[9] A. N. Jain, Surflex: fully automatic flexible molecular docking using a molecular similarity-based search engine. *J. Med. Chem.,* 46, 499-511 (2003).

We claim:
1. A pharmaceutical composition comprising a compound having a formula selected from the group consisting of

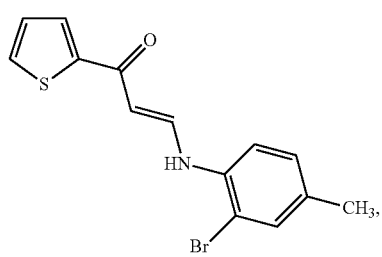

(II)

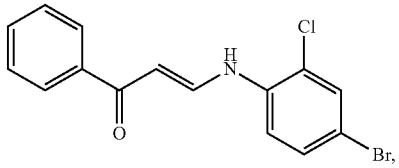

(III)

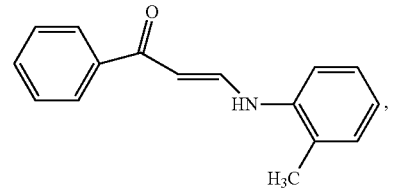

(IV)

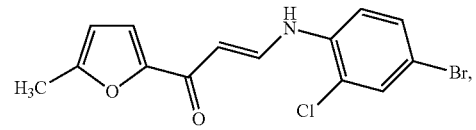

(V)

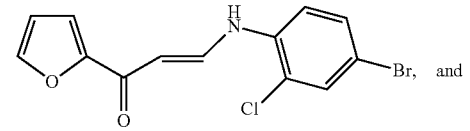

(VI)

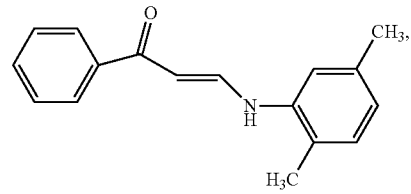

(VIII)

or a pharmaceutically acceptable salt thereof
and at least one pharmaceutically acceptable carrier, diluent and/or excipient.
2. The composition, according to claim 1, comprising a compound having Formula II, or a pharmaceutically acceptable salt thereof.
3. The composition, according to claim 1, comprising a compound having Formula III, or a pharmaceutically acceptable salt thereof.
4. The composition, according to claim 1, comprising a compound having Formula IV, or a pharmaceutically acceptable salt thereof.
5. The composition, according to claim 1, comprising a compound having Formula V, or a pharmaceutically acceptable salt thereof.
6. The composition, according to claim 1, comprising a compound having Formula VI, or a pharmaceutically acceptable salt thereof.
7. The composition, according to claim 1, comprising a compound having Formula VIII, or a pharmaceutically acceptable salt thereof.

* * * * *

UNITED STATES PATENT AND TRADEMARK OFFICE
CERTIFICATE OF CORRECTION

PATENT NO. : 9,750,717 B2
APPLICATION NO. : 15/019581
DATED : September 5, 2017
INVENTOR(S) : Esther Lutgens et al.

It is certified that error appears in the above-identified patent and that said Letters Patent is hereby corrected as shown below:

In the Specification

Column 4,
Line 25, "thereof" should read -- thereof. --.

Column 9,
Line 51, "4 and" should read -- 4 µm, and --.

Column 14,
Line 11, "(Abeam" should read -- (Abcam --.

Signed and Sealed this
First Day of May, 2018

Andrei Iancu
*Director of the United States Patent and Trademark Office*